US009138546B2

(12) United States Patent
Schubert et al.

(10) Patent No.: US 9,138,546 B2
(45) Date of Patent: Sep. 22, 2015

(54) SHIELDABLE NEEDLE ASSEMBLY WITH BIASED SAFETY SHIELD

(75) Inventors: Jakob Boegh Schubert, Graested (DK); Thibaud Hofstätter, Helsingoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 418 days.

(21) Appl. No.: 12/517,690

(22) PCT Filed: Nov. 23, 2007

(86) PCT No.: PCT/EP2007/062759
§ 371 (c)(1),
(2), (4) Date: Oct. 22, 2009

(87) PCT Pub. No.: WO2008/077706
PCT Pub. Date: Jul. 3, 2008

(65) Prior Publication Data
US 2010/0234811 A1    Sep. 16, 2010

Related U.S. Application Data

(60) Provisional application No. 60/878,574, filed on Jan. 4, 2007.

(30) Foreign Application Priority Data

Dec. 22, 2006   (EP) ..................................... 06126970

(51) Int. Cl.
*A61M 5/32*    (2006.01)
*A61M 5/34*    (2006.01)

(52) U.S. Cl.
CPC ............. *A61M 5/326* (2013.01); *A61M 5/3202* (2013.01); *A61M 5/347* (2013.01); *A61M 2005/3247* (2013.01); *A61M 2005/3267* (2013.01)

(58) Field of Classification Search
CPC ..................... A61M 5/326; A61M 2005/3267; A61M 2005/3247; A61M 5/3271; A61M 5/3257; A61M 5/3202; A61M 2005/325; A61M 5/321; A61M 5/50
USPC .............. 604/110, 251, 187, 93.01, 192, 197, 604/198
See application file for complete search history.

(56) References Cited

U.S. PATENT DOCUMENTS

| 4,664,654 A | 5/1987 | Strauss |
|---|---|---|
| 4,767,412 A | 8/1988 | Hymanson |

(Continued)

FOREIGN PATENT DOCUMENTS

| DE | 102004063603 | 7/2006 |
|---|---|---|
| EP | 216445 | 4/1987 |

(Continued)

OTHER PUBLICATIONS

English Abstract of DE 102004063603 Published Jul. 20, 2006.

*Primary Examiner* — Kevin C Sirmons
*Assistant Examiner* — William Carpenter
(74) *Attorney, Agent, or Firm* — Wesley Nicolas

(57) ABSTRACT

A needle assembly for an injection device comprising a needle cannula which is mounted in a hub connectable to an injection device, and a biasing shield which is telescopically guided relative to the hub between a position in which the needle cannula is covered and a position in which at least the sharp end of the needle cannula is exposed, such that an injection can be performed without visual contact with the needle cannula. Further releasable locking means is provided such that the user can lock or unlock the shield to perform the telescopi-cally movement. In order to release the shield, the injection device itself can be utilized as the key for unlocking.

10 Claims, 24 Drawing Sheets

(56) References Cited

U.S. PATENT DOCUMENTS

| | | | |
|---|---|---|---|
| 4,781,697 A | 11/1988 | Slaughter | |
| 4,795,432 A | 1/1989 | Karczmer | |
| 4,813,940 A | 3/1989 | Parry | |
| 4,894,055 A * | 1/1990 | Sudnak | 604/198 |
| 4,897,083 A * | 1/1990 | Martell | 604/192 |
| 4,911,693 A * | 3/1990 | Paris | 604/192 |
| 4,911,694 A | 3/1990 | Dolan | |
| 4,923,447 A * | 5/1990 | Morgan | 604/198 |
| 5,013,305 A | 5/1991 | Opie et al. | |
| 5,030,209 A | 7/1991 | Wanderer et al. | |
| 5,195,983 A | 3/1993 | Boese | |
| 5,242,416 A * | 9/1993 | Hutson | 604/192 |
| 5,292,314 A | 3/1994 | D'Alessio et al. | |
| 5,295,975 A * | 3/1994 | Lockwood, Jr. | 604/198 |
| 5,364,362 A * | 11/1994 | Schulz | 604/115 |
| 5,389,085 A * | 2/1995 | D'Alessio et al. | 604/198 |
| 5,415,645 A | 5/1995 | Friend | |
| 5,429,612 A | 7/1995 | Berthier | |
| 5,658,256 A | 8/1997 | Shields | |
| 5,688,241 A * | 11/1997 | Asbaghi | 604/110 |
| 5,741,236 A | 4/1998 | Kakiuti | |
| 5,769,826 A | 6/1998 | Johnson et al. | |
| 5,928,200 A | 7/1999 | Thorne et al. | |
| 5,941,857 A | 8/1999 | Nguyen et al. | |
| 5,984,899 A | 11/1999 | D'Alessio et al. | |
| 6,001,080 A | 12/1999 | Kuracina et al. | |
| 6,171,276 B1 * | 1/2001 | Lippe et al. | 604/67 |
| 6,190,361 B1 | 2/2001 | Gettig et al. | |
| 6,203,529 B1 * | 3/2001 | Gabriel et al. | 604/192 |
| 6,648,856 B1 * | 11/2003 | Argento | 604/192 |
| 6,679,864 B2 * | 1/2004 | Gagnieux et al. | 604/198 |
| 6,773,415 B2 * | 8/2004 | Heiniger | 604/110 |
| 6,986,760 B2 | 1/2006 | Giambattista et al. | |
| 7,361,160 B2 * | 4/2008 | Hommann et al. | 604/198 |
| 7,534,229 B2 * | 5/2009 | Hommann et al. | 604/187 |
| 7,553,293 B2 * | 6/2009 | Jensen et al. | 604/110 |
| 2003/0014019 A1 | 1/2003 | Saied | |
| 2003/0050606 A1 * | 3/2003 | Brand et al. | 604/197 |
| 2003/0149404 A1 | 8/2003 | Lehmann | |
| 2004/0199112 A1 | 10/2004 | Dalton | |
| 2005/0038392 A1 | 2/2005 | DeSalvo | |
| 2006/0089601 A1 | 4/2006 | Dionigi | |
| 2006/0184133 A1 | 8/2006 | Pessin | |

FOREIGN PATENT DOCUMENTS

| | | |
|---|---|---|
| EP | 216460 | 4/1987 |
| EP | 279583 A2 | 8/1988 |
| EP | 364839 A1 | 4/1990 |
| EP | 409180 | 1/1991 |
| EP | 903157 | 3/1999 |
| EP | 1032446 | 5/1999 |
| EP | 1466638 A2 | 10/2004 |
| EP | 1289587 | 8/2005 |
| EP | 1448256 | 1/2006 |
| JP | H1052492 A | 2/1998 |
| JP | 2003010326 A | 1/2003 |
| JP | 2003-525087 A | 8/2003 |
| JP | 2006-521141 A | 9/2006 |
| WO | 92/13585 A1 | 8/1992 |
| WO | WO 99/25402 | 11/1998 |
| WO | WO 01/76665 | 10/2001 |
| WO | WO 01/91837 | 12/2001 |
| WO | WO 01/93928 | 12/2001 |
| WO | WO 02/20074 | 3/2002 |
| WO | WO 03/045480 | 7/2003 |
| WO | WO 03/066141 | 8/2003 |
| WO | 2004/004812 A1 | 1/2004 |
| WO | WO 2005/018722 | 3/2005 |
| WO | 2005035029 A1 | 4/2005 |
| WO | WO 2005/035029 | 4/2005 |
| WO | WO 2005/079889 | 9/2005 |
| WO | 2006/032385 A1 | 3/2006 |
| WO | 2008/077706 A1 | 7/2008 |
| WO | 2008107199 A1 | 9/2008 |

* cited by examiner

SHIELDABLE NEEDLE ASSEMBLY WITH BIASED SAFETY SHIELD

CROSS-REFERENCE TO RELATED APPLICATIONS

This application is a 35 U.S.C. §371 national stage application of International Patent Application PCT/EP2007/062759 (published as WO 2008/077706), filed Nov. 23, 2007, which claimed priority of European Patent Application 06126970.0, filed Dec. 22, 2006; this application further claims priority under 35 U.S.C. §119 of U.S. Provisional Application 60/878,574, filed Jan. 4, 2007.

THE TECHNICAL FIELD OF THE INVENTION

The invention relates to a needle assembly and especially to a needle having a shielded needle cannula.

DESCRIPTION OF RELATED ART

Needle assemblies are commonly used to either inject substances into or extract substances out of human or animal bodies. Such needle assemblies are typically disposable and are discarded after use. The problem presented by the disposal of a needle assembly, and indeed, by any handling of the needle assembly, is the potential risk of being injured by the sharp end of the needle cannula. This is particular dangerous when following after the penetration of a patients skin since the needle cannula then may be contaminated and therefore capable of spreading diseases such as hepatitis and HIV.

A great number of needle assemblies have been developed where the needle cannula is concealed by a spring loaded and telescopically movable shield during the injection. These needle assemblies can be divided into two different kinds of needles assemblies.

The first kind is often referred to as safety needles and has a spring loaded shield which covers the sharp end of the needle cannula both before injection, during injection and especially after injection. Such safety needle further has irreversible locking means locking the shield in the position covering the needle cannula after only one injection. Such safety needles are disclosed in e.g. WO 03/066141, EP 1.289.587 and in EP 1.448.256.

A second kind of shielded needle is disclosed in WO 99/25402 and in WO 01/76665. The shield disclosed is telescopically movable against the force of a spring located between the hub and the shield. This needle assembly has no irreversible lock and can therefore be used for multiple injections in the same way as a common non-shielded injection needle.

As it is apparent from WO 99/25402 such injection needle is ready for injection at any time, however the same kind of needle assembly which can be used for multiple injections can also be made in a way requiring the user to actively unlock the shield prior to each injection. Such needle assembly is disclosed in WO 01/76665. Here the locking element must be moved into a new axial track prior to each injection by applying an axial pressure on the shield.

Instead of attaching the shield to the hub as in the previous examples, WO05/035029 discloses an injection pen with a common non-shielded injection needle and an auxiliary shield-mechanism forming part of the injection pen.

It is henceforth a problem with injection needle assemblies that any person handling the needle is in a potential risk of being accidentally injured by the needle. For the second type of needle assemblies that do not lock after injection there is also a danger for persons handling the needle assembly after it has been discarded.

Thus, there is a need for a needle assembly that can provide a higher degree of safety against accidental needle stick injuries in more situations.

DESCRIPTION OF THE INVENTION

It is an object of the present invention to provide a needle assembly having a shielded needle cannula which can be locked or unlocked dependent on the situation of use.

The shield is constantly urged in the distal direction by the biasing means such that the tip of the needle cannula is covered. When the needle assembly is in its unlocked position it is possible to telescope the shield in the proximal direction which is preferably done by pressing the shield against the skin of the user during injection. In the locked position, the shield is prevented from telescoping. The releasable locking means cooperates with the connecting means such that the locking means are only released upon activation of the connecting means. When the locking means cooperates with the connecting means to be released when the connecting means are activated it is possible for a user to use the injection device to unlock the shield such that when a user connects the needle assembly to the injection device the needle assembly is automatically unlocked whereas when it is removed from the injection device it is automatically locked again. As a result of this the needle assembly is always locked when dismounted and unlocked when mounted.

It is however also possible to make it such that the needle assembly can be manually shifted between a locked and an unlocked mode when mounted, whereas it is always locked when dismounted.

The connecting means which is usually a thread connection or a bayonet coupling is normally located at the proximal end of the hub ready to be connected to an injection device. The releasable locking means is usually provided with a number of activating parts or extensions which protrudes into the area of the connecting means such that the activating parts are activated when an object such as an injection device enters into the connecting area and interfaces the connecting means.

Further a separate locking element can be provided. The activating means are preferably provided on the locking element which is moved from the locking to the unlocking position by activation from the injection device. The movement of the locking element can either be rotational or axial or a combination thereof. Preferably, a thread connection secures that the locking element is rotated when it is axially moved, in this way the locking element can be moved to a new rotational position as it is axially moved e.g. by the injection device.

The needle assembly and injection pen together forms a system were it is assured that the safety shield can only be telescoped once the needle assembly is mounted on the injection device, further it is also assured that when the needle assembly is dismounted the shield covering the needle cannula is locked such that a user can not come into contact with the sharp end on the needle cannula.

In addition to this an overriding locking mechanism can be provided such that the safety shield can be shifted between a locked and an unlocked position only when the needle assembly is mounted on an injection device.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

The term "Needle Cannula" is used to describe the actual conduit performing the penetration of the skin during injection. A needle cannula is usually made from a metallic material and connected to a hub to form an injection needle. A needle cannula could however also be made from a polymeric material or a glass material. The hub which carries the connecting means for connecting the injection needle to an injection apparatus is usually moulded from a suitable thermoplastic material.

"Cartridge" is the term used to describe the container containing the insulin. Cartridges are usually made from glass but could also moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the insulin which is pressed out as the plunger decreased the volume of the space holding the insulin.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be constructed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula penetrating the patient whereas the term "proximal end" is meant to refer to the opposite end pointing away from the patient in a situation of use.

Example 1

FIG. 1-2

Figure 1:
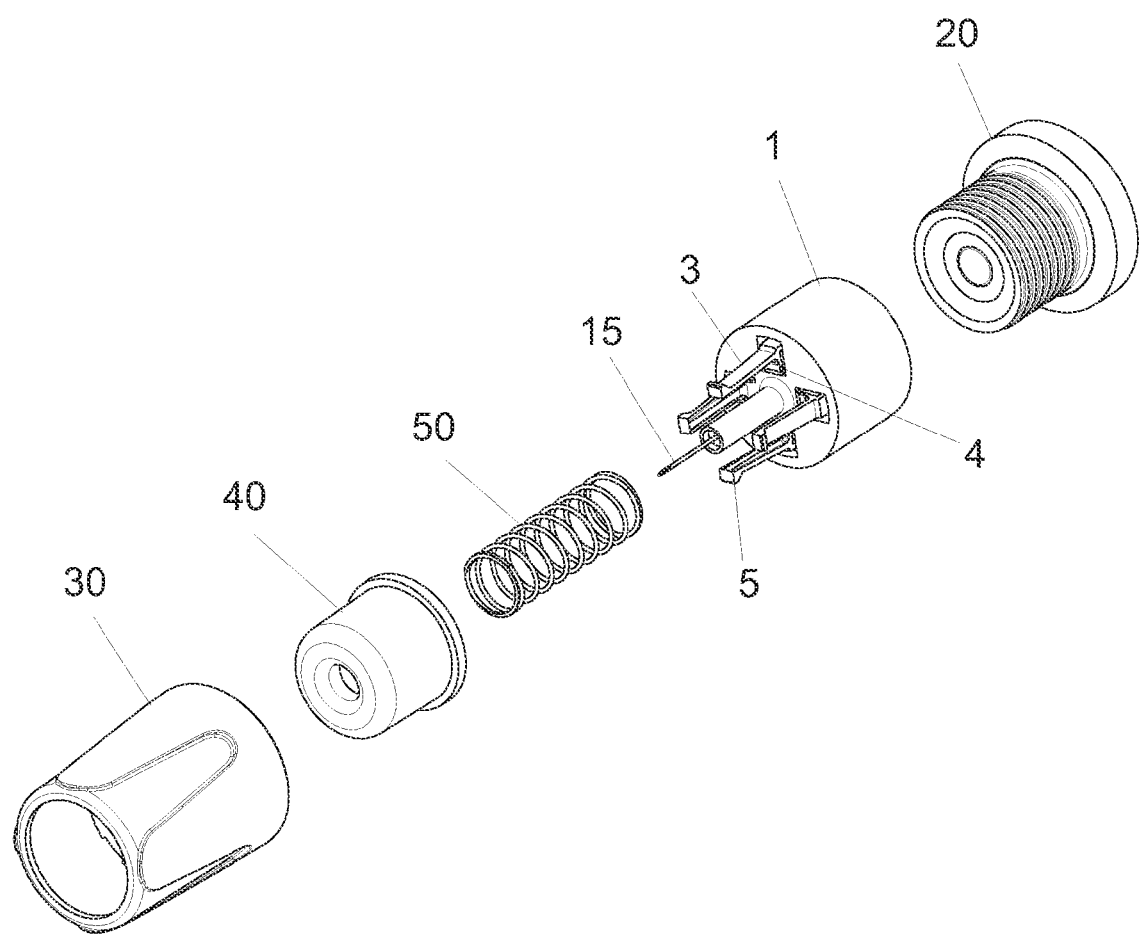
FIG. 1 Show an exploded view of an example of a hidden needle assembly.

FIGS. 1 and 2 discloses a hub 1 carrying a needle cannula 15. In use the needle cannula 15 forms a conduit between the interior of a cartridge 25 secured in an injection device 20 and the subcutaneous layer of a user. The hub 1 is surrounded by an outer shield 30 which is permanently connected to the hub 1 e.g. by snapping, gluing or welding the two parts 1, 30 together, alternatively the two parts 1, 30 can be formed as one part during moulding.

The hub 1 is further provided with interior coupling means 2 such as a thread or one or more protrusions for a bayonet coupling as described in EP 1,536,854. These engagement means 2 co-operates with similar engaging means 21 on the distal end of the injection device 20 in order to secure the hub 1 to the injection device 20.

Although the term "injection device" is used through out this application, a Penfill® equipped with an adapter top to fit into a Novo Nordisk pen system according to U.S. Pat. No. 5,693,027 or similar containers with drugs provided with connecting means for a needle assembly is also considered to fall under this term.

The needle cannula 15 has a distal end 16 with a sharp point for penetrating the skin of the user and a proximal end 17 for penetrating into the cartridge 25 holding the drug to be injected.

The outer shield 30 is provided with a rim 31 bordering an opening 32 at the distal end. A safety shield 40 which preferably is provided with a rib 41 is prevented from falling out the opening 32 due to the engagement between the rim 31 and the rib 41.

A resilient element 50 such as a spring is located between the safety shield 40 and the hub 1, urging the safety shield 40 in the distal direction whereby the safety shield 40 covers the distal end of the needle cannula 10.

The hub 1 is on its distal side provided with a number of arms 3 extending in the distal direction. These arms 3 are secured to the remaining part of the hub 1 by film hinges 4 such that the arms 3 can move flexible in a radial direction. The arms 3 could also be provided on a separate element which could be attached to the hub 1 e.g. by snapping, gluing or welding. The most distal end of these arms 3 is preferably provided with a shoulder 5. The proximal side of the film hinges 4 is further provided with a proximally pointing protrusion 6 located radically displaced to the axial axis of the arms 3.

Figure 2A:
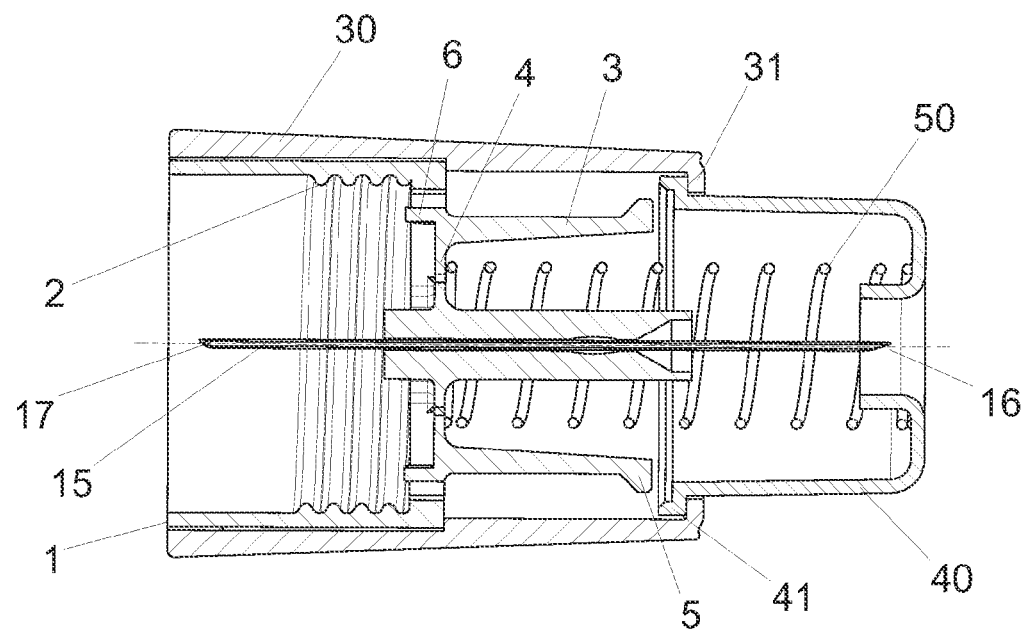
FIG. 2 A-B Show a cross section of the hidden needle assembly of FIG. 1.

In the initial position shown in FIG. 2A, the safety shield 40 is pressed forward by the spring 50 and the shoulder 5 on the arms 3 is positioned directly beneath the shield 40. Due to the abutment between the shoulders 5 and the safety shield 40 it is not possible to telescope the safety shield 40 in the proximal direction.

Figure 2B:
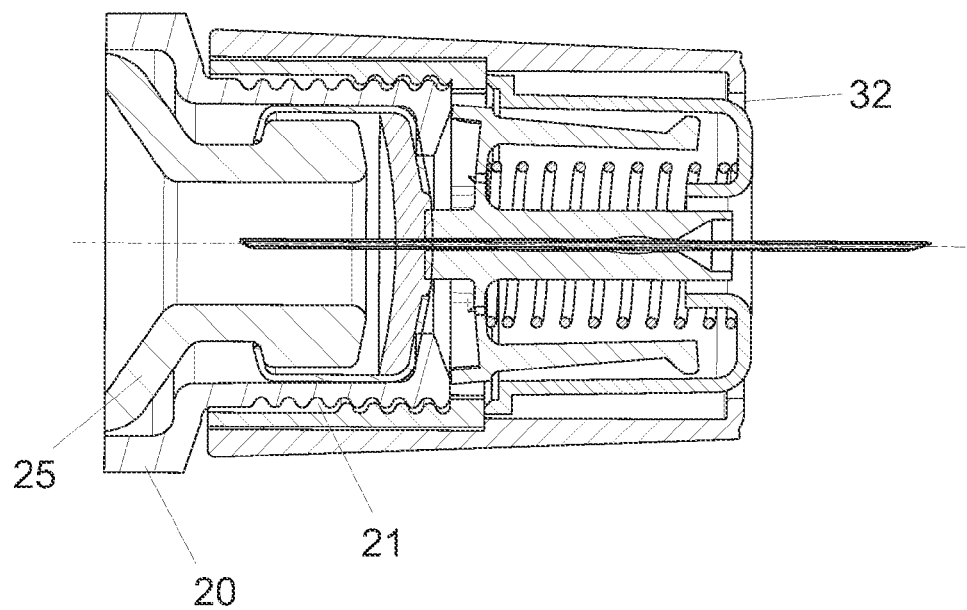

When the injection device 20 is inserted into the hub 1 and secured in position as shown in FIG. 2B, the distal end of the injection device 20 abuts the protrusions 6. This distally working pressure on the protrusions 6 makes the flexible film hinge 4 flex whereby the arms 3 and its shoulders 5 are moved inwardly toward the centre of the needle assembly due to the dislocated position of the protrusions 6. This radial movement of the arms 3 and its shoulders 5 removes the shoulders 5 from its abutment with the safety shield 40, which is hereafter movable in its axial direction.

When the injection has been finalized and the needle hub 1 is removed from the injection device 20, the pressure is released from the protrusions 6. This will make the flexible film hinge 4 flex back to its initial position where the arms 3 once again will be situated right beneath the safety shield 40 preventing axial movement of the safety shield 40. Due to this mechanism, the safety shield 40 is only axially movable when connected to the injection device 20.

Example 2

FIG. 3-4

Figure 3:
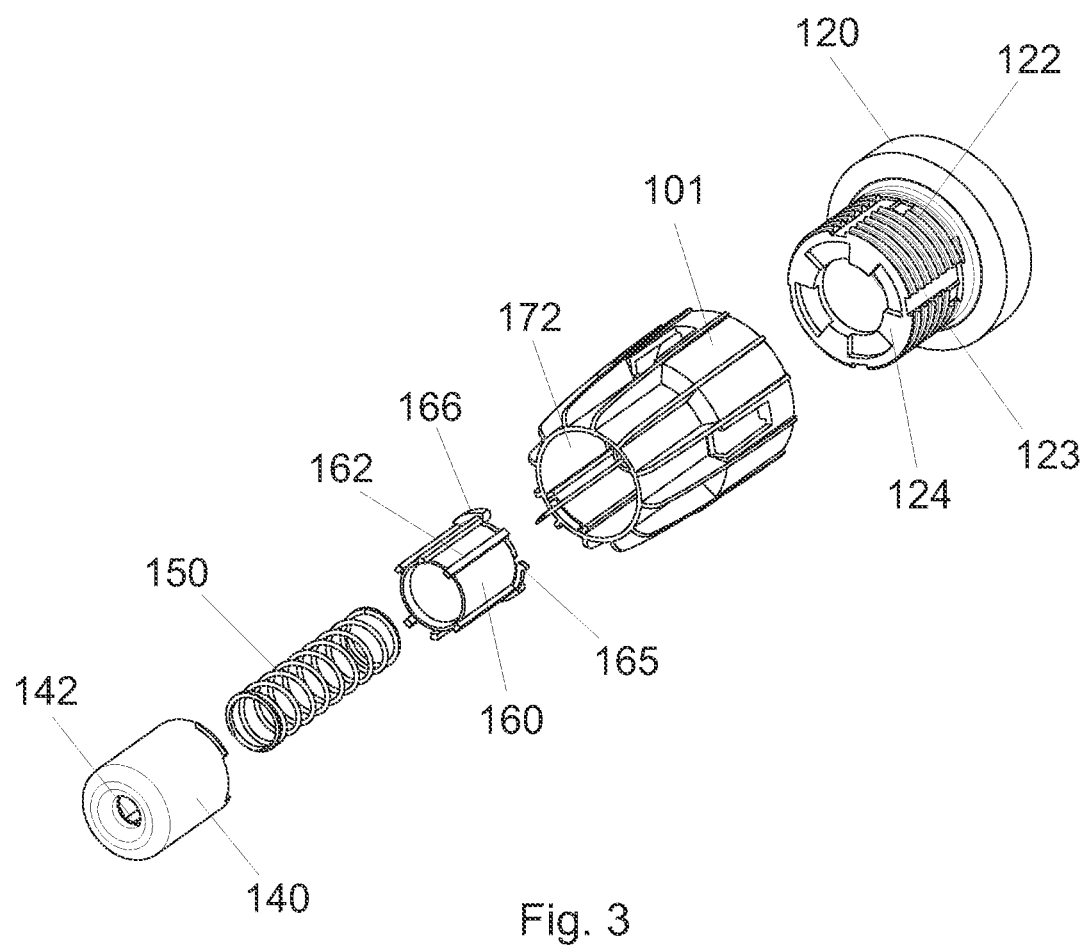
FIG. 3 Show an exploded view of an example of a hidden needle assembly.
Figure 4A:
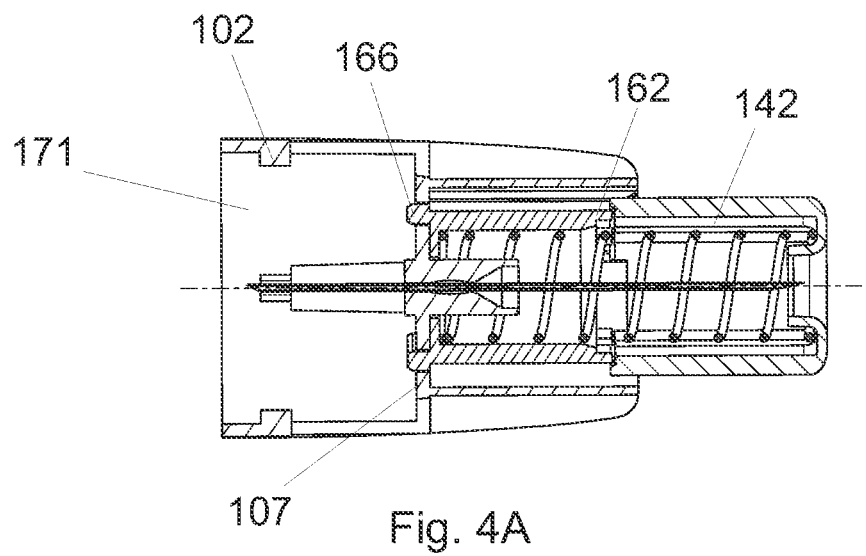
FIG. 4 A-C Show a cross section of the hidden needle assembly of FIG. 3.
Figure 4B:
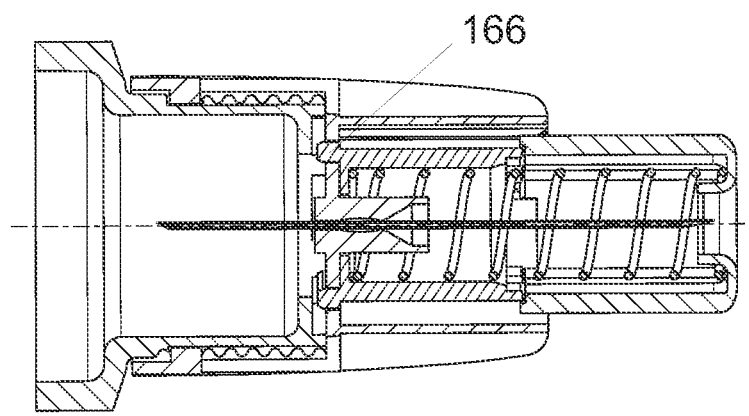
Figure 4C:
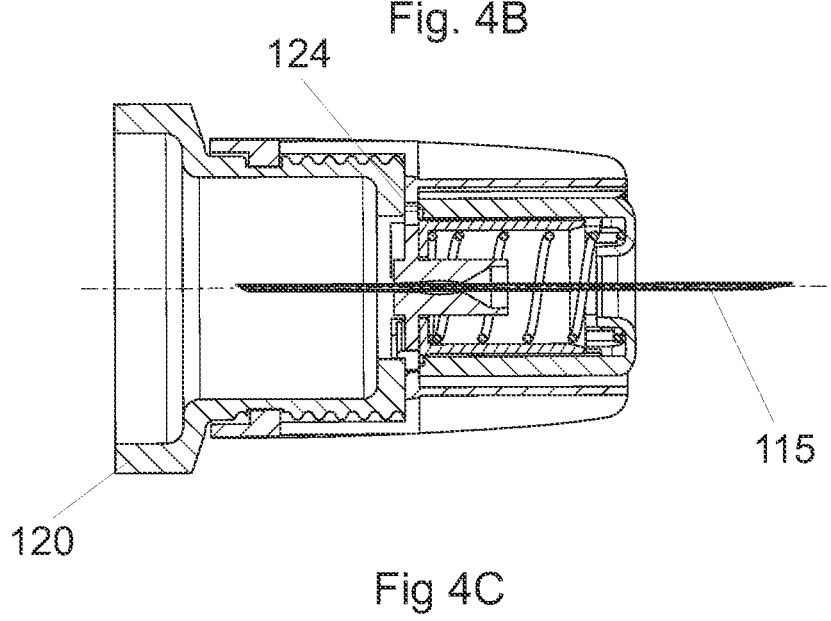

In a different example disclosed in FIGS. 3 and 4 the hub 101 carrying the needle cannula 115 is connected with the outer shield or alternatively moulded as one piece. A spring 150 is located between the hub 101 and the safety shield 140 urging the safety shield 140 in the distal direction. The inside surface of the safety shield 140 is provided with a number of raised ribs 142 which extends in the longitudinal direction. These ribs 142 can be formed in a multitude of different ways e.g. as protrusions.

Similar ribs or protrusions 162 are formed on the exterior surface of a locking element 160. The locking element 160 is located inside the hub 101 and abuts the hub 101 proximally. Also proximally, the locking element 160 is provided with a number of fingers 166 which extends into the connecting area 171 of the hub 101.

The hub 101 is divided into two areas by a partition 107. The first area being the safety shield guiding area 172 and the second area being the connecting area 171 which is provided with means 102 for coupling the hub 101 to an injection device 120. The injection device 120 and the hub 101 could also be provided with combined thread 122 and bayonet 123 coupling as described in EP 1.536.854. As could a broad variety of different ways of mounting the needle assembly on the injection device 120 be foreseen e.g. different snap or click-on mechanisms.

In this embodiment the injection device 120 is preferably provided with a number of distally located knobs 124. These knobs 124 interact with the fingers 166 of the locking element 160. When the hub 101 is connected to the injection device 120, the injection device 120 and the hub 101 is usually rotated relatively to each other, the extend of the rotation depends of the type of connection. A threaded connection demands several full rotations where a bayonet coupling usually demands less than one full rotation. The situation just before the knobs 124 on the injection device 120 encounters the fingers 166 on the locking element is disclosed in FIG. 4B. At the end of the rotational movement between the hub 101 and the injection device 120 as depictured in FIG. 4C, the knobs 124 engages the fingers 166 of the locking element 160 forcing the locking element 160 to rotate. In order for the knobs 124 to abut properly to the fingers 166 a bayonet coupling or a steep thread is preferred.

The longitudinal ribs or protrusions 142 of the safety shield 140 are in the initial position located aligned with the similar ribs or protrusions 162 on the locking element 160. In this way the safety shield 140 is prevented from axial movement. When the locking element 160 is rotated the ribs or protrusion 142, 162 disengages and makes it possible to move the safety shield 140 in a telescopic movement as disclosed in FIG. 4C.

Once the user releases the hub 101 from the injection device 120 by rotating in the opposite direction, the position of the knobs 124 on the injection device 120 and the fingers 166 on the locking element 160 is designed such that the fingers 166 and thereby the locking element 160 is returned to the initial and locked position. The injection device 120 could e.g. be equipped with four knobs 124 as disclosed. When mounting the needle assembly to the injection device, the forefront of the knops 124 in the rotational direction abuts the fingers 166, whereas when the needle assembly is dismounted the backfront of the next knob 124 abuts the finger 166 at its opposite end.

In order to prevent unintentional rotational movement between the locking element 160 and the hub 101 e.g. during transportation, a reversible click-arm 165 could be guided in a not shown track inside the hub 101. This could also serve the purpose of providing the user with a sound signal.

Example 3

FIG. 5-6

Figure 5:
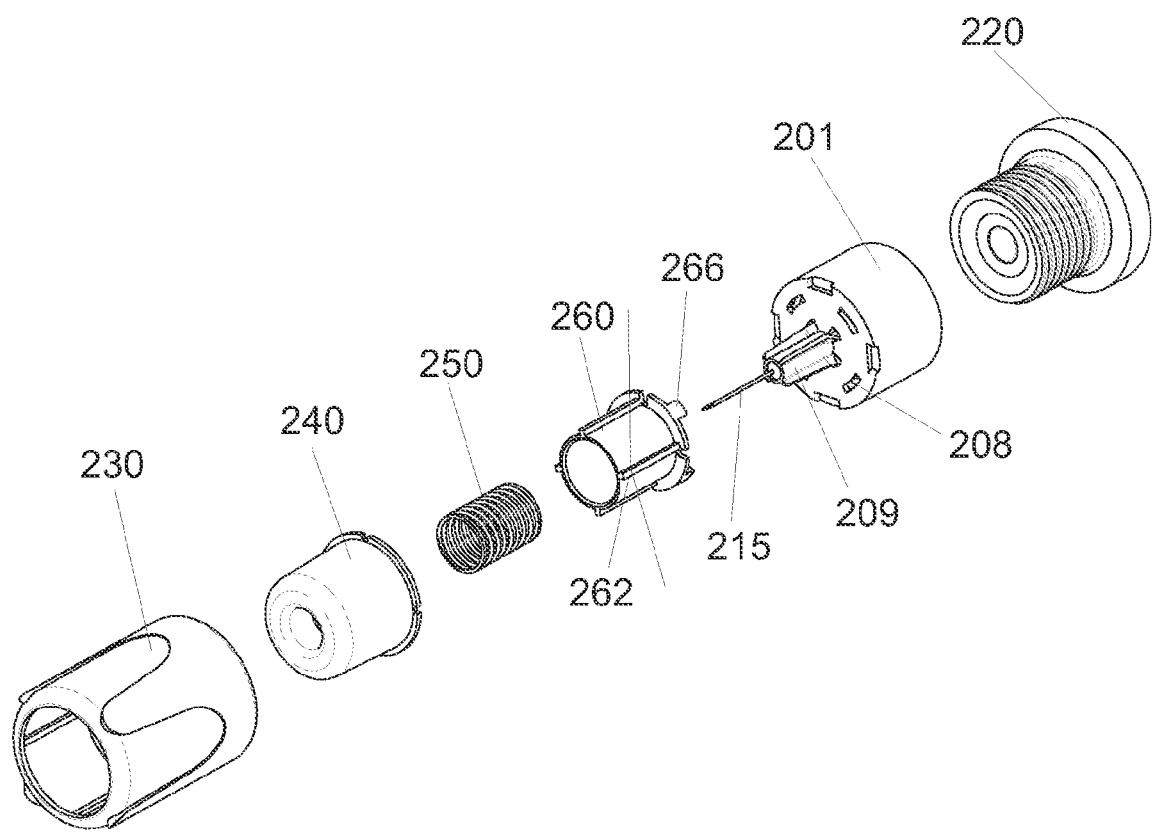
FIG. 5 Show an exploded view of an example of a hidden needle assembly.

A similar embodiment is disclosed in FIGS. 5 and 6. The hub 201 is provided with an internal thread 202 for connecting the hub 201 carrying the needle cannula 215 to an injection device 220. An outer shield 230 is attached to the hub 201 or alternatively moulded in one piece with the hub 201. The hub 201 is further provided with a centrally located tower 209 inside which the needle cannula 215 is glued to the hub 201. This tower 209 is provided with an external thread 210. A locking element 260 having an internal thread 261 surrounds the tower 209 and is threadedly engaged with the external thread 210 on the tower 209. Alternatively an internal thread could be provided on the inside surface of the outer shield 230 engaging an external thread provided on the outside surface of the locking element 260.

The locking element 260 is further provided with a number of protrusions 266 which extends in a proximal direction through openings 208 in the base portion of the hub 201 and into the hollow part 271 of the hub 201 housing the internal threads 202. All though internal threads 202 are disclosed in the figures they could be replaced by a bayonet coupling without interfering with the way of operating the disclosed needle assembly.

Figure 6A:
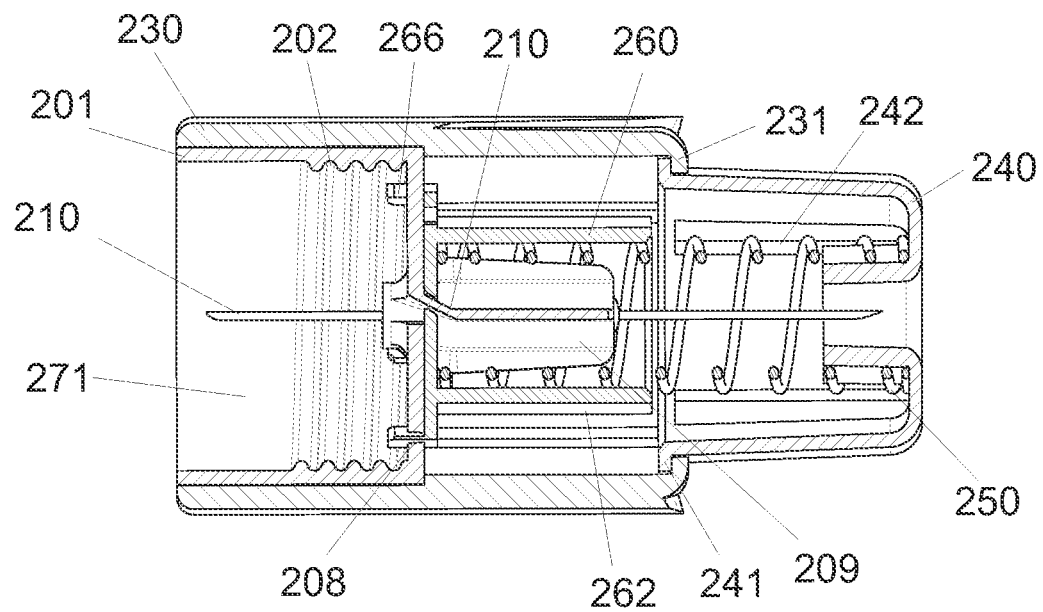
FIG. 6 A-B Show a cross section of the hidden needle assembly of FIG. 5.

A resilient element disclosed as a spring 250 is interfaced between the locking element 260 and the shield 240 urging the shield 240 in the distal direction and urging the locking element 260 in the proximal direction such that the locking element 260 in the initial position disclosed in FIG. 6A abuts the hub 201.

The locking element 260 is on its outside surface equipped with a number of axially extending ribs 262 and the shield 240 is on its inside surface provided with similar inwardly pointing ribs 242. In the initial position the axially extending ribs 262 of the locking element 260 abuts the inwardly pointing rib 242 of the shield 240 thereby preventing the rib from telescoping relatively to the hub 201.

Figure 6B:
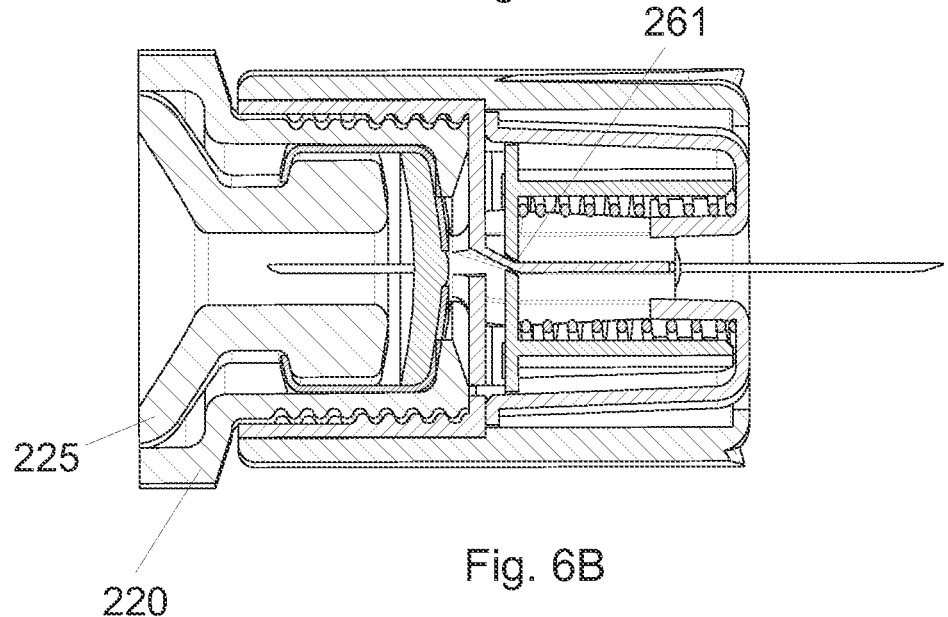

When the hub 201 is attached to an injection device 220 having a cartridge 225 as disclosed in FIG. 6B, the distal end of the injection device 220 will press the protrusions 266 on the locking element 260 through the holes 208 of the hub 201 and lift the locking element 260 out of abutment with the hub 201. Due to the threaded connection 210, 261 between the locking element 260 and the tower 209 of the hub 201, the locking element 260 will be rotated during its axial movement. This rotation will cause the axially extending ribs 262 on the locking element 260 to be dislocated in relation to the inwardly pointing ribs 242 on the shield 240 thereby allowing the shield 240 to move in an axial direction relatively to the hub 201.

It is evident that the axial extending ribs 262 and the inwardly pointing ribs 242 could be formed in many different ways, The function that the two elements 242, 262 abuts each other in one position but are free of each other when rotated can be accomplished in many different ways e.g. by forming the ribs as protrusions or the like.

When the hub 201 is disconnected from the injection device, the spring 250 will urge the locking element 260 in the proximal direction which will cause the locking element 260 to be rotated back to the locked position. In this way the shield 240 is only allowed to telescope when the hub 201 is mounted on the injection device 220.

Example 4

FIG. 7-8

Figure 7:
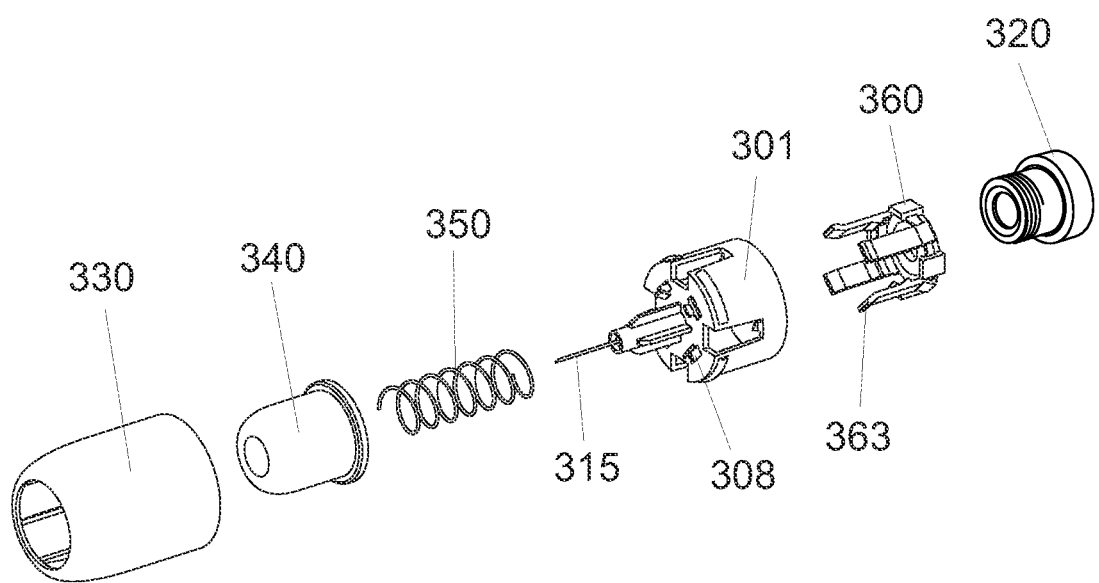
FIG. 7 Show an exploded view of an example of a hidden needle assembly
Figure 8A:
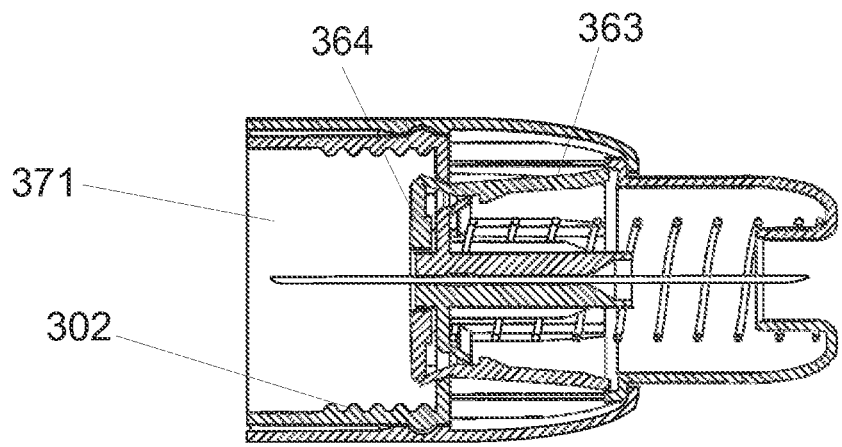
FIG. 8 A-C Show a cross section of the hidden needle assembly of FIG. 6.
Figure 8B:
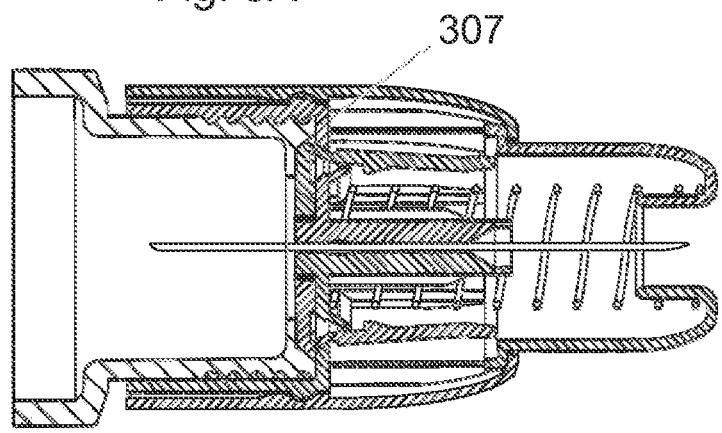
Figure 8C:
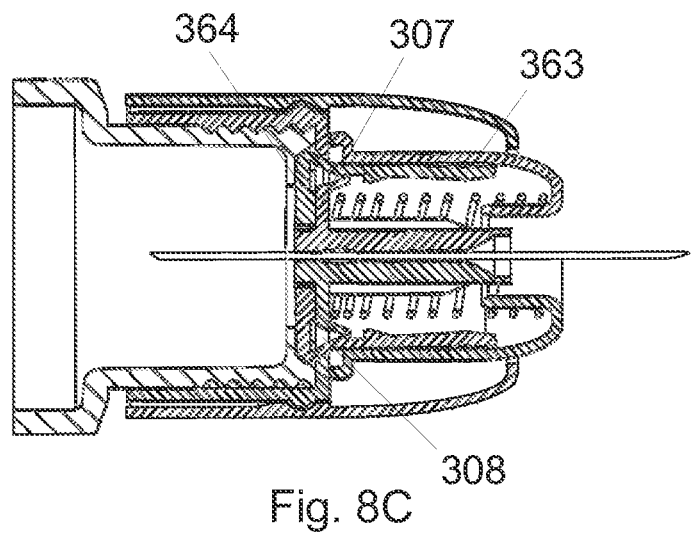

In the embodiment depictured in FIGS. 7 to 8, the axial movement of the locking element 360 forces the arms 363 to move in a radial direction in and out of engagement with the safety shield 340.

A spring 350 is mounted between the hub 301 and the safety shield 340. In addition the spring 350 could apply pressure on the locking element 360 urging it in the proximal direction as explained below.

The locking element 360 has a number of arms 363 provided on a base 364 located in the connecting area 371 of the hub 301 having threads 302, the arms 363 extends into the area distal to the hub 301 through openings 308 in the partition 307. The geometry of the openings 308 in the partition 307 and the arms 363 is such that the arms 363 are forced to move in a radial direction when the locking element 360 is axially moved.

When the hub 301 carrying the needle cannula 315 is connected to the injection device the pressure applied on base 364 of the locking element 360 by the injection device 320 forces the locking element 360 to move in the distal direction which again forces the arms 363 to move in a radial direction towards the centre of the needle assembly thereby bringing the arms 363 out of engagement with the safety shield 340. Once the arms 363 do no longer abut the safety shield 340, the safety shield 340 can be moved telescopically in the proximal direction as disclosed in FIG. 8 B-C making it possible to perform an injection.

When the hub 301 is removed form the injection device, the geometry and elasticity of the arms 363 and partitions 307 forces the locking element 360 back into its initial position whereby the arms 363 are moved radial outward to a position beneath the safety shield 340 thereby preventing further movement of the safety shield 340. The returning of the locking element 360 could also be assisted by not-shown arms on the base 364 penetrating through openings in the hub 301, which not-shown arms would then be acted upon by the spring 350.

Example 5

FIG. 9-10

Figure 9:
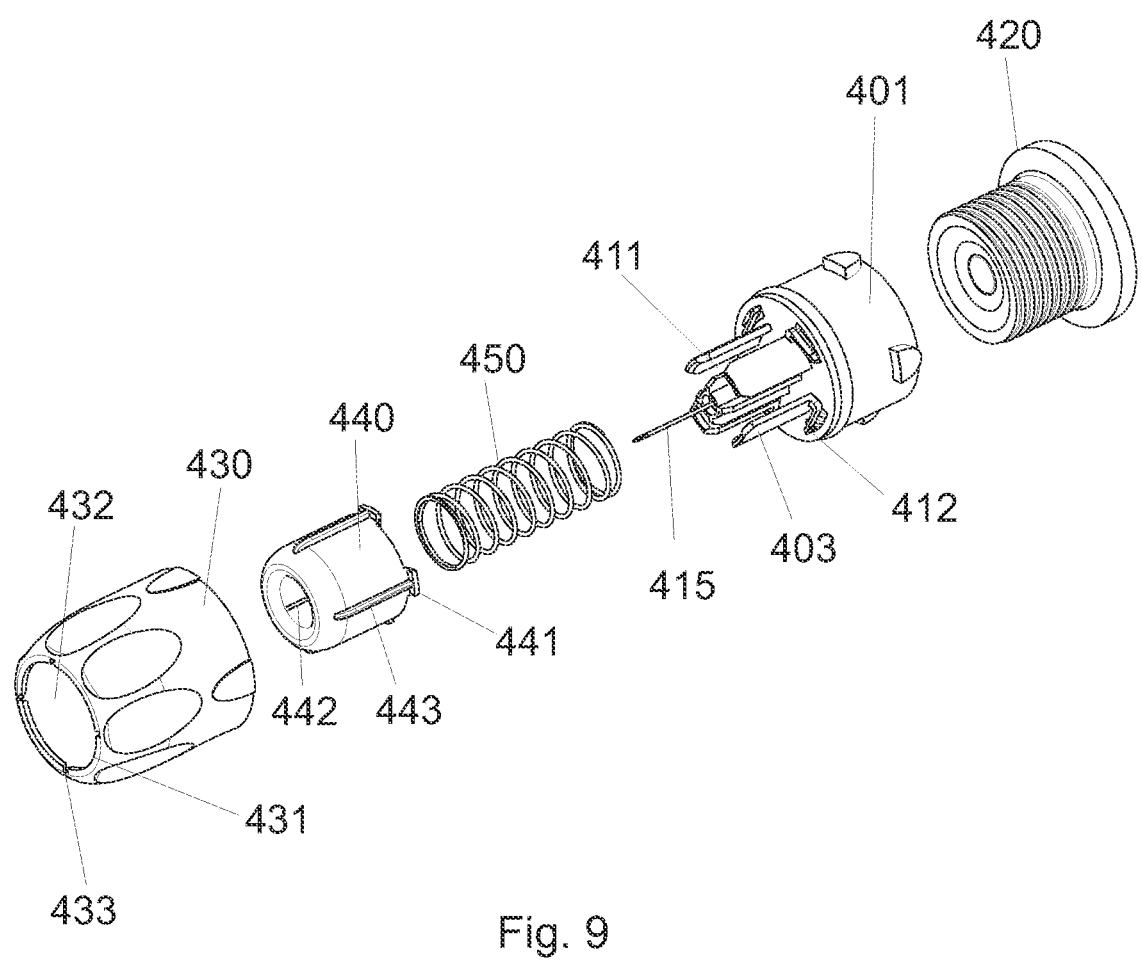
FIG. 9 Show an exploded view of an example of a hidden needle assembly.
Figure 10A:
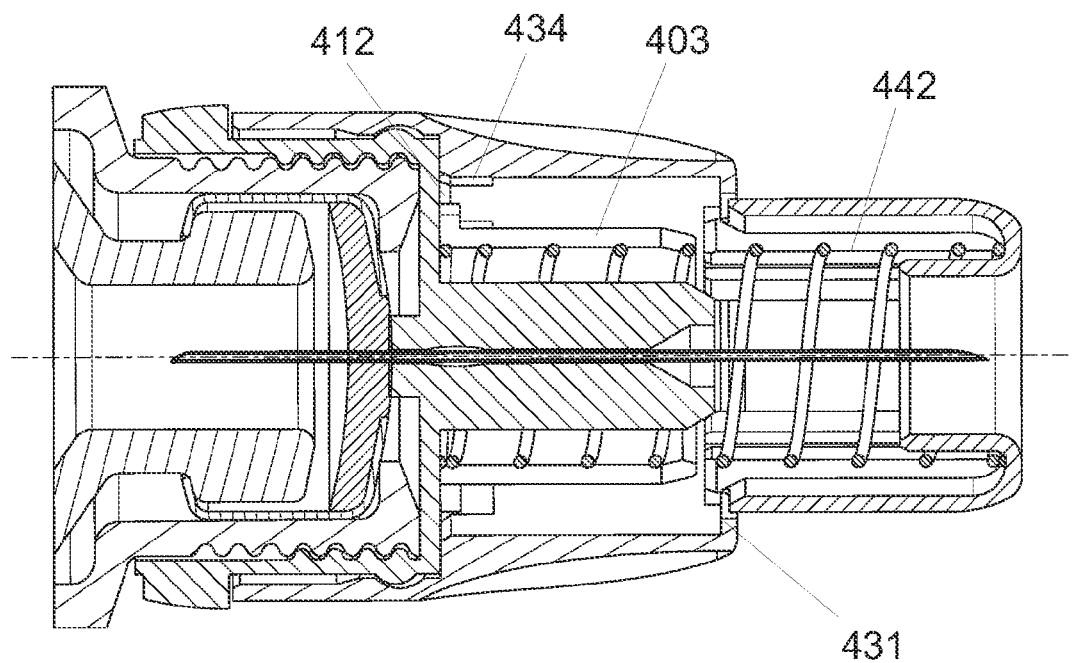
FIG. 10 A-B Show a cross section of the hidden needle assembly of FIG. 9.
Figure 10B:
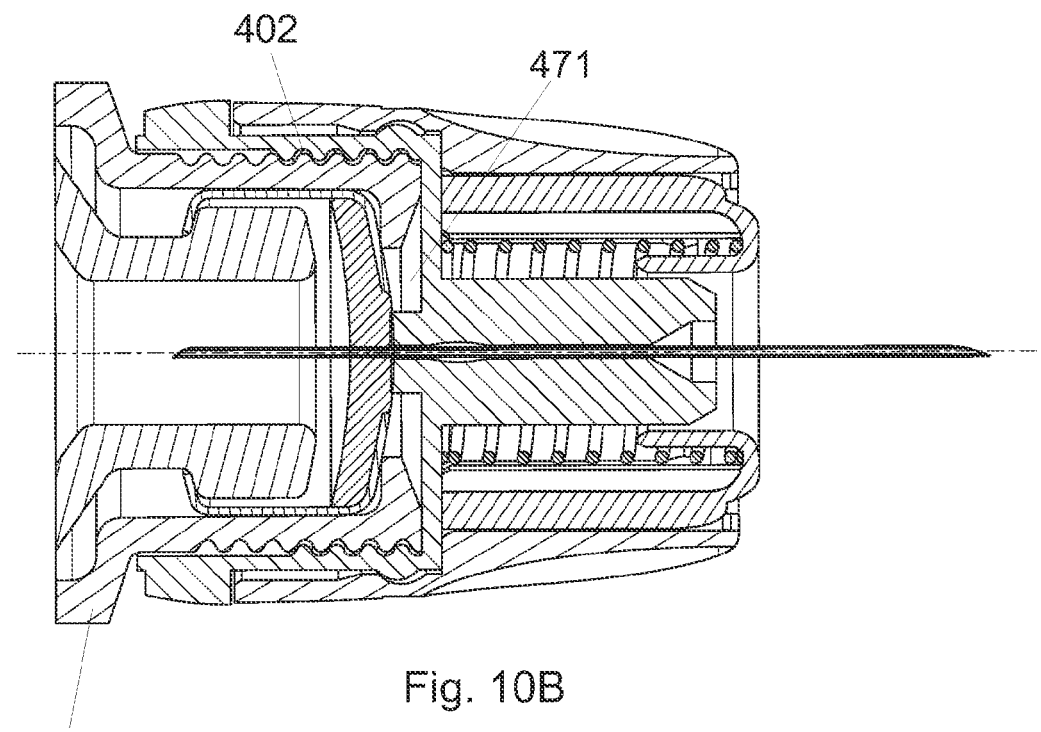

In the example disclosed in FIG. 9-10, the hub 401 carrying the needle cannula 415 is provided with a number of distally extending arms 403. In-between the arms 403 open slots 411 are provided. Further the hub 401 is provided with suitable connecting means 402 for connecting the needle assembly to an injection device.

On the external surface of the hub 401 a rotational outer shield 430 is provided. This shield 430 can rotate relatively to the hub 401, which is further provided with a number of click-arms 412 which engages a toothed track 434 on the inside surface of the outer shield 430 such that this can only rotate in one direction relatively to the hub 401.

The outer shield 430 is further provided with a number of guiding slits 433 guiding similar guiding ribs 443 on the outside of the safety shield 440.

A spring 450 is located between the hub 401 and the safety shield 440 urging the safety shield 440 in the distal direction. Protrusions 441 on the safety shield 440 interact with a rim 431 on the outer shield 430 thereby preventing the safety shield 440 from be pressed out the opening 432 of the outer shield 430.

The safety shield 440 is further provided with a number of inwardly pointing ribs 442 on its inside surface.

In the initial position disclosed in FIG. 10A the ribs 442 on the inside surface of the safety shield 440 is positioned above the arms 403 provided on the hub 401. This alignment prevents the safety shield 440 form axial movement.

When a user rotates the outer shield 430 relatively to the hub 401, the safety shield 440 is forced to rotate due to the engagement between the guiding slits 433 on the outer shield 430 and the guiding ribs 443 on the outside of the safety shield 440. This rotational movement rotates the inwardly pointing ribs 442 out of engagement with the arms 403 and into a position above the open slots 411 provided between the arms 403. In this position the inwardly pointing ribs 442 of the safety shield 440 is free to move telescopically in the slots 411. The click arms 412 and the toothed track 434 on the inside of the outer shield 430 control the rotational movement. When four arms 403 are present as disclosed in the FIGS. 9-10, then the rotational movement between locked on unlocked position would be 45 degrees, however a different number of arms 403 and inwardly pointing ribs 442 can be used.

In order to lock the safety shield 440, the user simply rotates the outer shield 430 and the safety shield 440 to its next position in which the inwardly pointing ribs 403 once again is positioned aligned with the arms 403.

In this way a user can shift the needle assembly between its locked and its unlocked mode simply by rotating the outer shield 430 relatively to the hub 401 no matter if the needle assembly is mounted on an injection device 420 or not.

Example 6

FIG. 11-13

Figure 11:
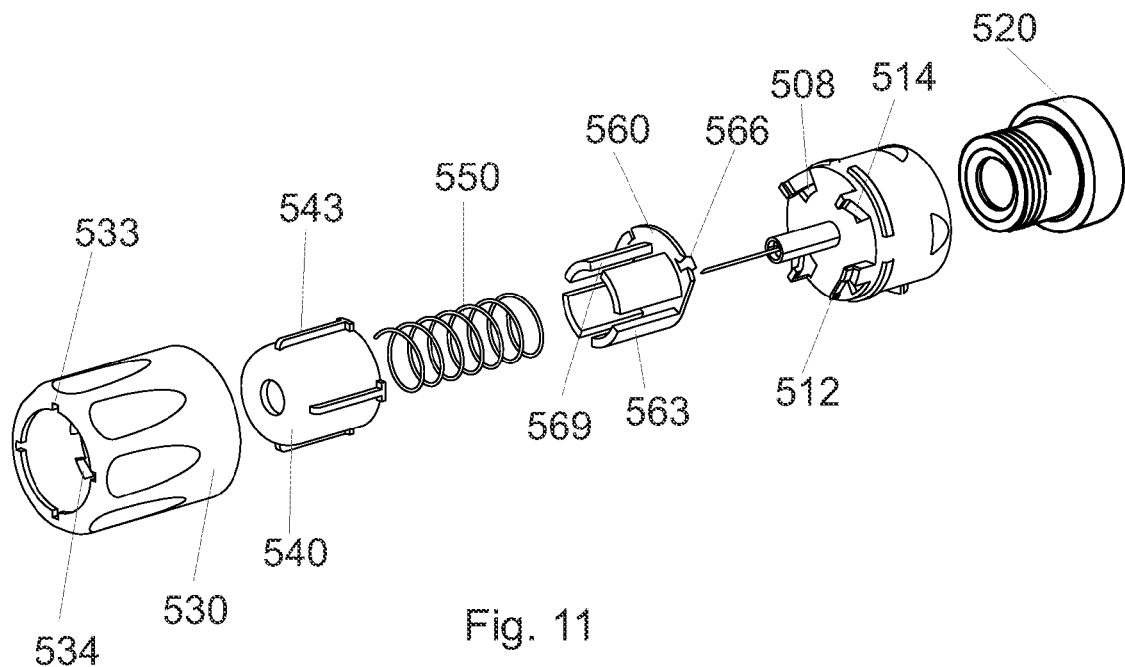
FIG. 11 Show an exploded view of an example of a hidden needle assembly.
Figure 12:
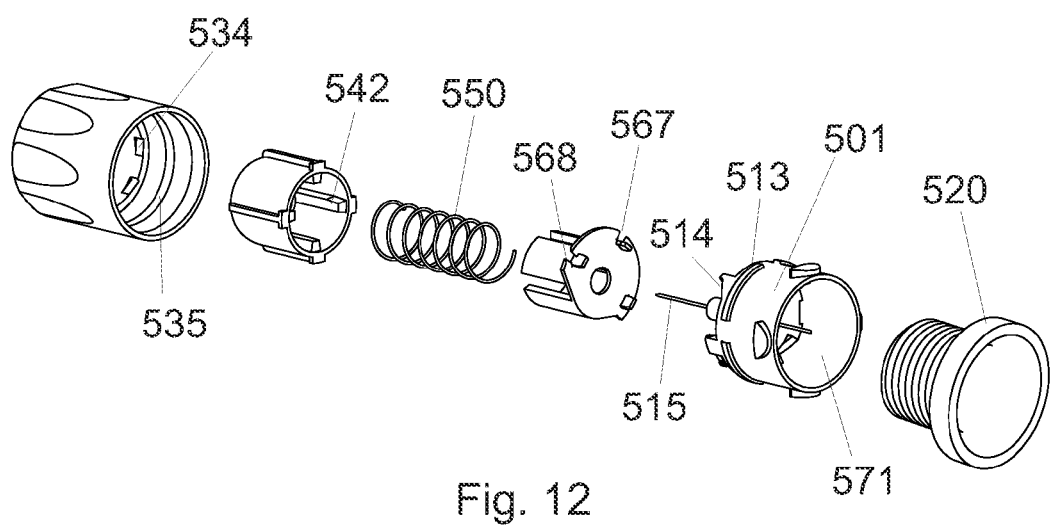
FIG. 12 Show an exploded view of the hidden needle assembly of FIG. 11.

An example very similar to the previous is disclosed in the FIGS. 11-13. Here the rotational outer shield 530 engages the safety shield 540 by the guiding slits 533 engaging the guiding ribs 543 on the outside surface of the safety shield 540.

Figure 13A:
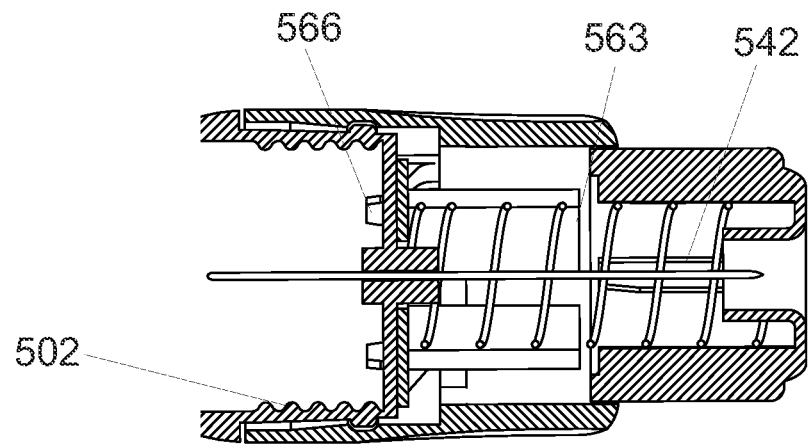
FIG. 13 A-C Show a cross section of the hidden needle assembly of FIGS. 11 and 12.

The arms 563 obstructing the telescopically movement of the safety shield 540 is provided on a separate locking element 560 which in the initial position disclosed in FIG. 13A prevents axial movement of the safety shield 540. Longitudinal slots 569 are provided between the arms 563.

The outer shield 530 is rotational mounted on the hub 501 carrying the needle cannula 510 by a groove 535 in the outer shielded 530 engaging a similar raised ring 513 on the hub 501, and the rotational movement is controlled by the click arms 512 and the track 534 inside the outer shield 530. The hub 501 is further provided with suitable connecting means 502 for connecting the needle assembly to an injection device 520. However, when the needle assembly is not mounted on an injection device 520 the locking element 560 is urged by the spring 550 into a position where it abuts the hub 501, and in this position depictured in FIG. 13A the inwardly pointing ribs 542 of the safety shield 540 is positioned above the arms 563 such that the safety shield 540 is prevented from telescopically movement. The interaction between the click arms 512 and the track 534 is such that when the outer shield 530 is moved into its next guided position the inwardly pointing ribs 542 move to a position above the next arm 563. So no matter in which guided position the outer shield 530 (and the safety shield 540) is, no telescopically movement is allowed.

The locking element 560 is further provided with a number of fingers 566 which extend through openings 508 into the connecting area 571 such that the injection device 520 presses on the protrusion 566 when the needle assembly is mounted.

The locking element 560 is on its proximal side provided with cut-away parts 567 carrying a sloping edge 568. This sloping edge 568 abuts a similar sloping protrusion 514 provided on the distal side of the hub 501.

Figure 13B:
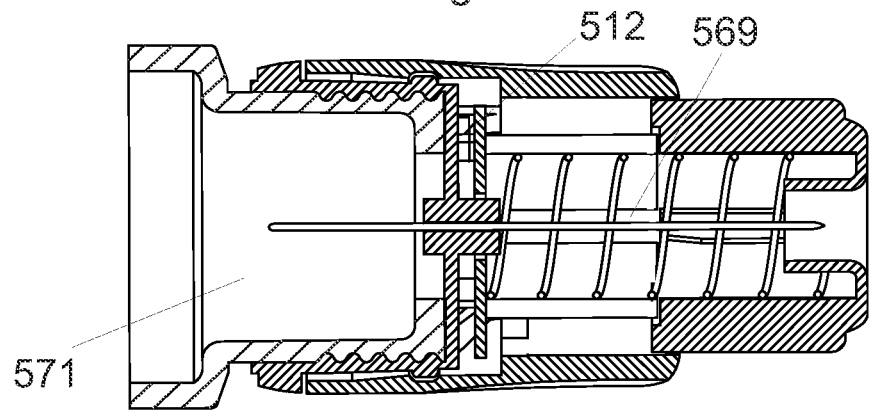
Figure 13C:
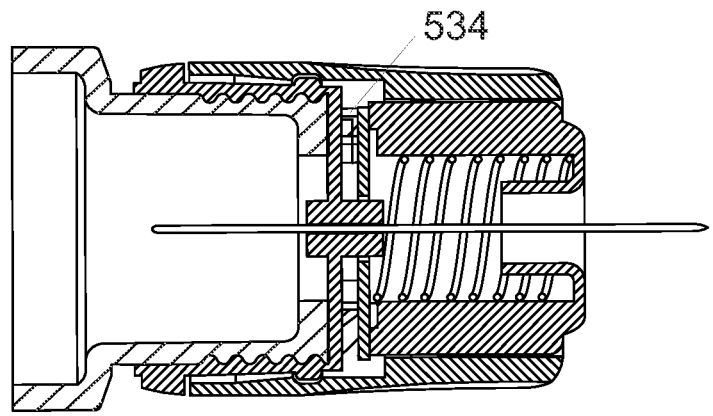

When a user mounts the needle assembly on an injection device 520 as depictured in FIGS. 13B and 13C, the injection devices 520 presses the locking element 560 in the distal direction. Due to engagement between the sloping edge 568 of the locking element 560 and the sloping protrusion 514 on the hub 501, the locking element 560 rotates relatively to the hub 501 as it is moved distally.

This rotation moves the arms 563 and the slots 569 to a new position in which the arms 563 is located such relatively to the inwardly pointing ribs 542 on the safety shield 540 that the safety shield 540 can be shifted from a position in which the arms 563 are aligned with the inwardly pointing ribs 542 and a position where the inwardly pointing ribs 542 is aligned with the slots 569. This means that once the needle assembly is mounted on the injection device 520 the user can rotate the outer shield 530 guided by the click arms 512 and the track 534 such that the safety shield 540 shifts between a locked and an unlocked position. As disclosed in the FIGS. 11 and 12 the slots 569 can be 90 degrees apart form each other in which case the outer shield 530 is moved 45 degrees in each rotation such that it shifts between locked and unlocked positions. However when the needle assembly is not mounted on an injection device 520 the inwardly pointing ribs 542 and the slots 569 are dislocated such that the inwardly pointing ribs 542 can never be in a position above a slot 569. In this way it is secured that the position in which the safety shield 540 can telescope only can be obtained when the needle assembly is mounted on the injection device 520. Once the needle assembly is dismounted the relative position between the arms 563 and the inwardly pointing ribs 542 are such that the safety shield 540 can never telescope, the inwardly pointing ribs 542 will be above an arm 563 no matter in which guided position the outer shield 530 (and the safety shield 540) is in. It is understood that the location of the shiftable positions in the track 534 and the relative location of the inwardly pointing ribs 542 inside the safety shield 540 and the arms 563 and slots 569 are decisive for this.

Example 7

FIG. 14-15

Figure 14:
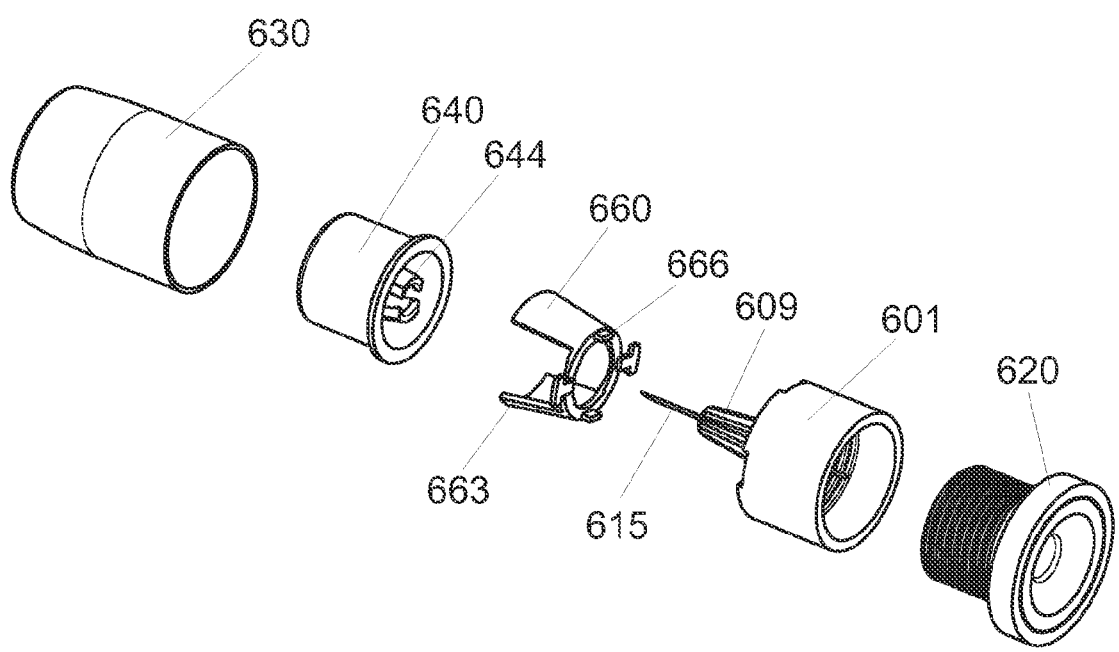
FIG. 14 Show an exploded view of an example of a hidden needle assembly.
Figure 15:
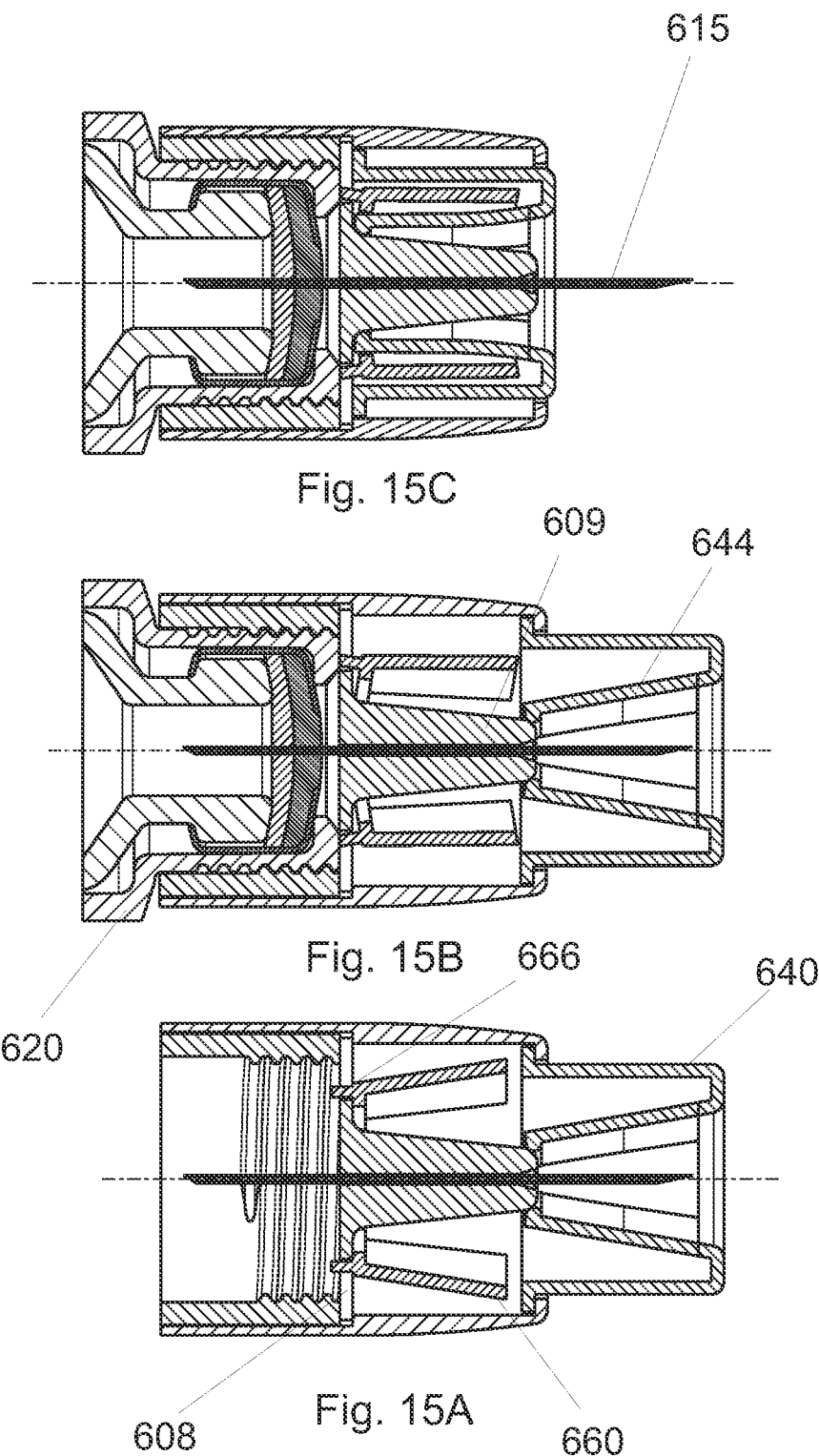
FIG. 15 A-C Show a cross section of the hidden needle assembly of FIG. 14.

In the embodiment depictured in the FIGS. 14-15 no spring element as such is included. The hub 601 carries the needle cannula 615, and a separate locking element 660 is provided between the hub 601 and the safety shield 640 which parts are encapsulated in the outer shield 630.

The locking element 660 is further provided with fingers 666 which protrude through holes 608 in the hub 601.

When the hub 601 is mounted on an injection device 620, the distal end of the injection device 620 presses on the fingers 666 which makes the arms 663 of the locking element 660 deflect inwardly allowing the safety shield 640 to axially pass the locking element 660 as depictured in FIGS. 15B and 15C.

The safety shield 640 is internally provided with a plurality of conical flanges 644 which in use slides on the tower 609. These conical flanges 644 replaces the spring member in the forgoing embodiments and works as the biasing means urging the safety shield 640 to the first position once the needle cannula 615 is retracted from the skin. In order to enhance the biasing force the tower 609 of the hub 601 slopes towards its distal end, further when the hub 601 is removed from the injection device 620 the flexibility of the base of the locking element 660 urges it back to its first position and the safety shield 640 is moved to its first position.

Example 8

FIG. 16-17

Figure 16:
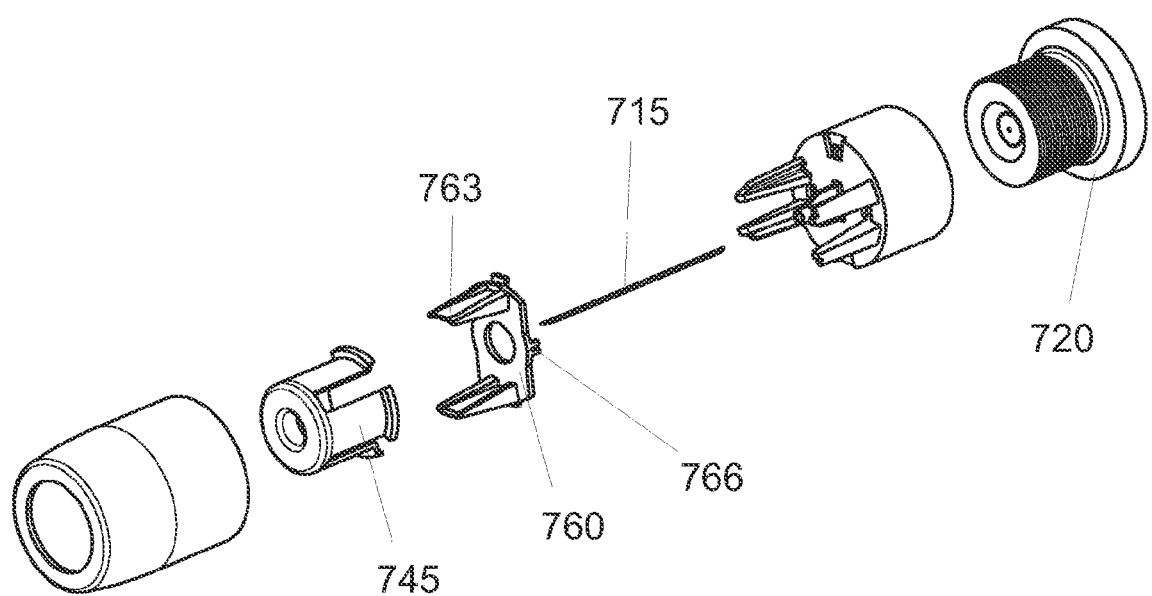
FIG. 16 Show an exploded view of an example of a hidden needle assembly.
Figure 17C:
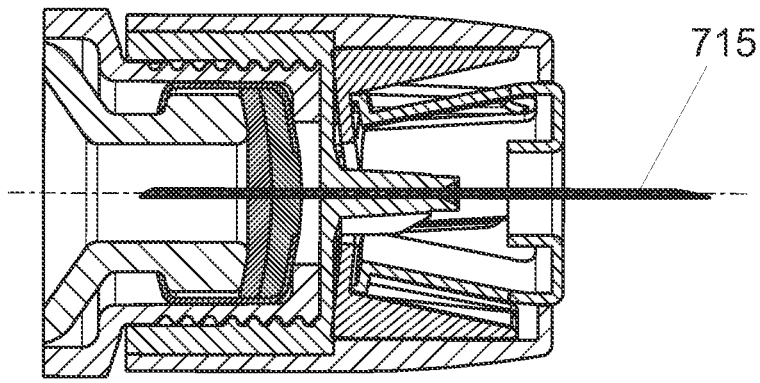
FIG. 17 A-C Show a cross section of the hidden needle assembly of FIG. 16.
Figure 17B:
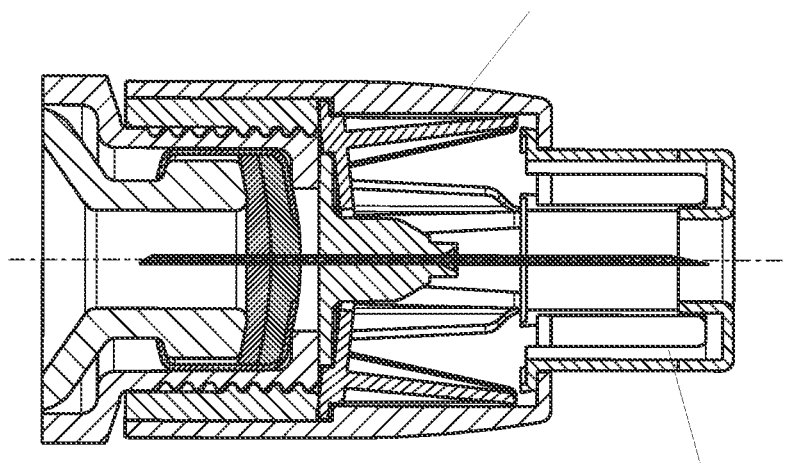
Figure 17A:
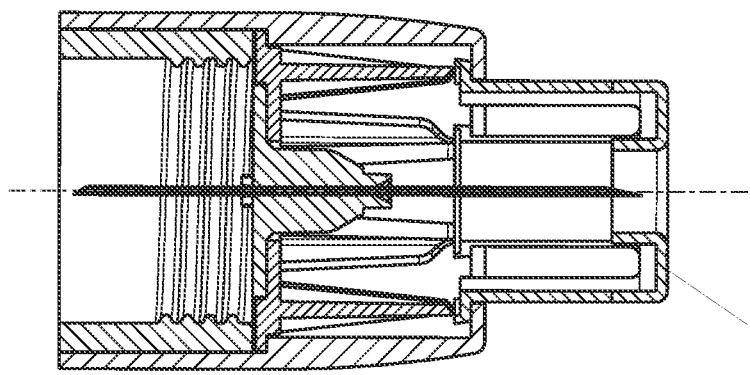

In the embodiment depictured in the FIGS. 16 and 17, the arms 763 on the locking element 760 deflect outwardly when the fingers 766 are activated by the injection device 720. When the arms 763 are outwardly deflected as depictured in FIG. 17B, the safety shield 740 is allowed to axially pass the locking element 760.

Further the skirt of the safety shield 740 is divided into a plurality of skirt parts 745 which are pressed inwardly by the arms 763 of the locking element 760 when the safety shield 740 is moved to the position uncovering the needle cannula 715. The arms 763 forms a conical sloping surface on the interior when deflected outwardly as depictured in the FIGS. 17B and 17C. The inwardly pressing of the skirt parts 745 on the conical sloping surface operates as a biasing mean urging the safety shield 740 back to its secured position when the needle cannula 715 is removed from injection site, further when the hub 701 is removed from the injection device 720 the flexibility of the base of the locking element 760 urges it back to its first position and the safety shield 740 is moved to its first position.

Example 9

FIG. 18-19

Figure 18:
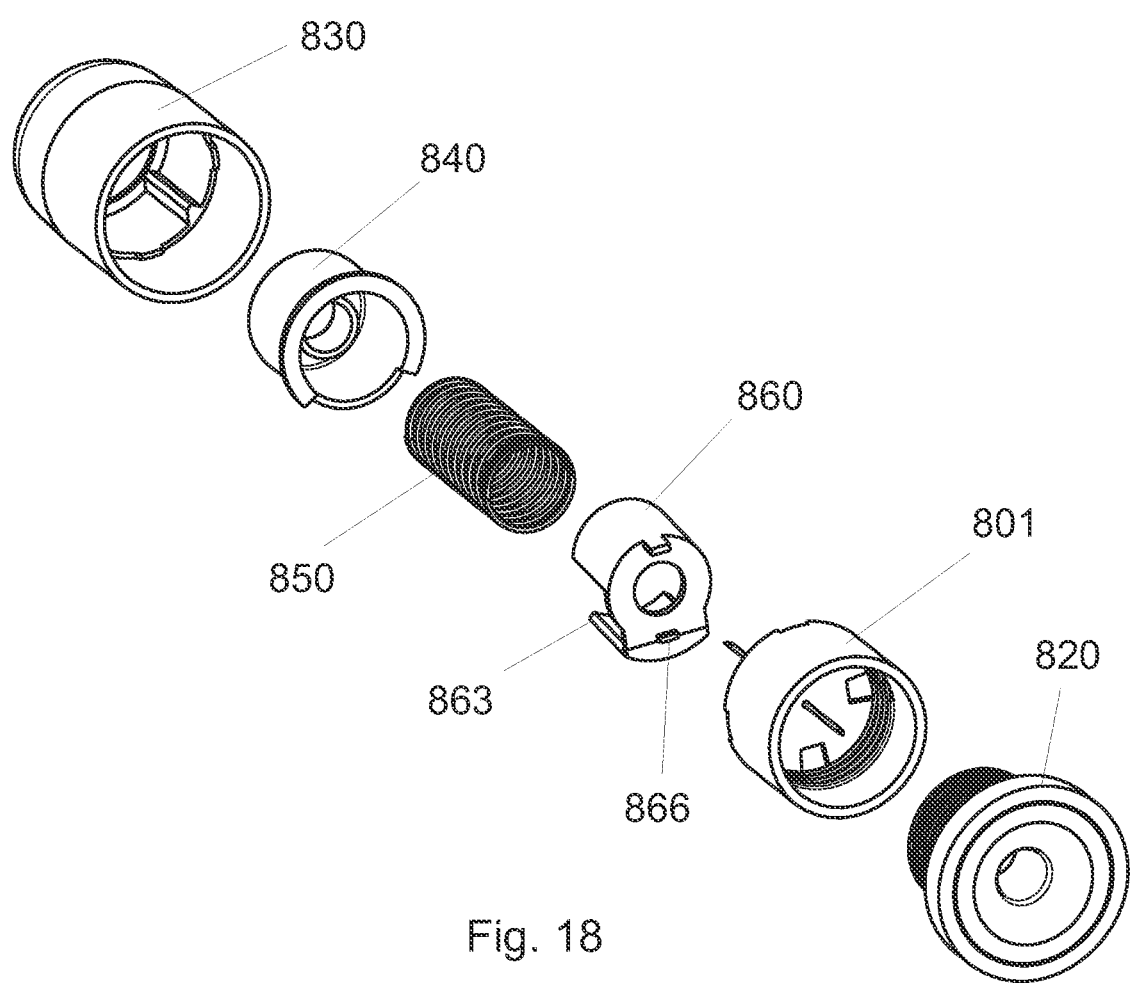
FIG. 18 Show an exploded view of an example of a hidden needle assembly.
Figure 19C:
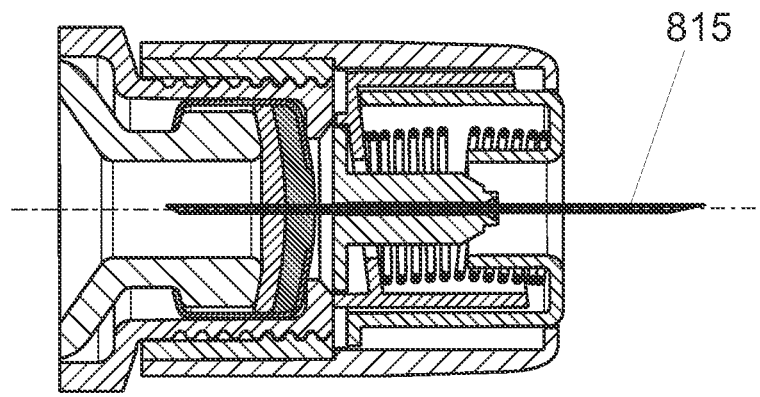
FIG. 19 A-C Show a cross section of the hidden needle assembly of FIG. 18.
Figure 19B:
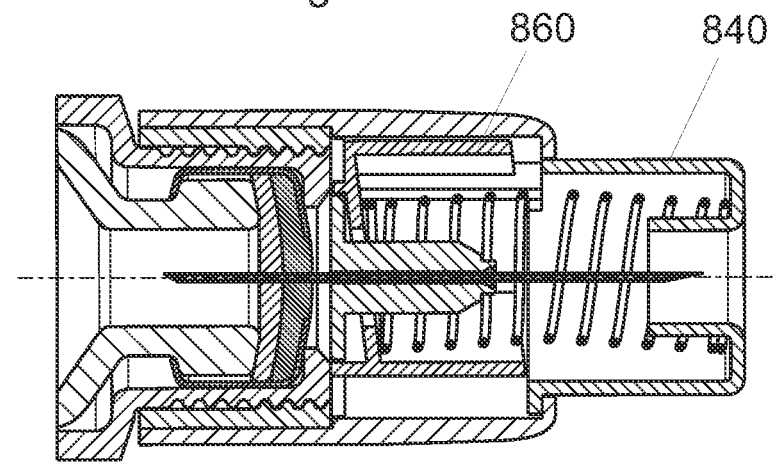

FIGS. 18 and 19 discloses an embodiment in which the needle cannula 815 is attached to the hub 801, further an outer shield 830 is attached to the hub 810. Internally of the outer shield 830, a safety shield 840 and a locking element 860 is provided with a spring 850 urging the two parts 840, 860 from each other, The locking element is provided with a finger 866 stretching through a hole 808 in the hub 801 and into the connecting area 871 of the hub 801.

Figure 19A:
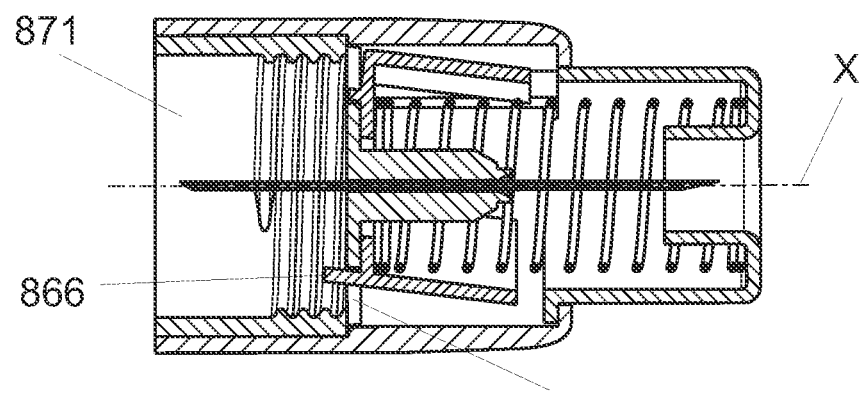

The locking element 860 is provided with a number of arms 863 which forms an angle with the axial axis X of the needle assembly as depictured in FIG. 19A. In this non-activated position, the safety shield 840 is prevented from axial movement by the arms 863 of the locking element 860. When an injection device 820 is attached to the connecting area 871, the finger 866 of the locking element 860 is activated and the locking element 860 is forced into a position in which the arms 863 is aligned with the axial axis X of the needle assembly as depictured in FIG. 19B. In this position the safety shield 840 can move freely in the axial direction.

Example 10

FIG. 20-21

Figure 20:
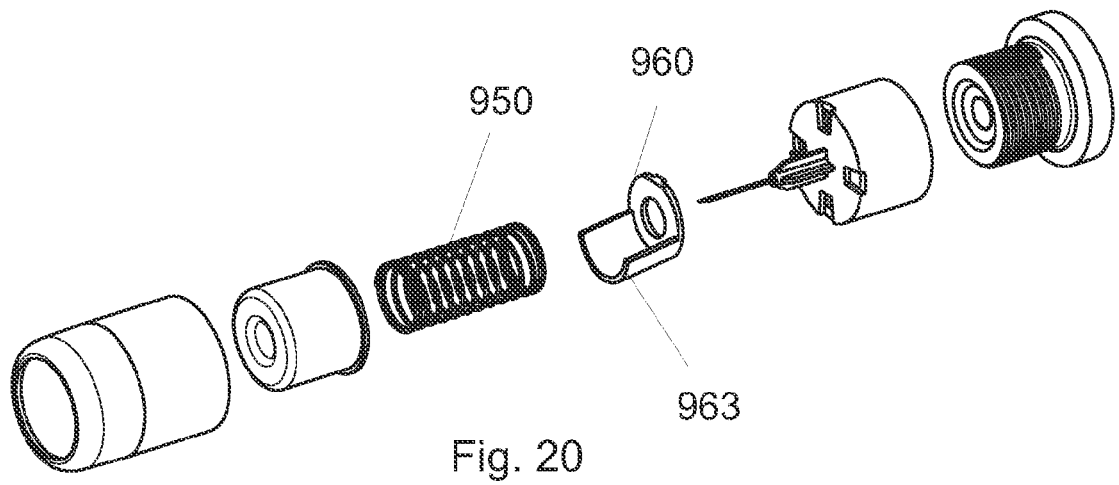
FIG. 20 A-B Show an exploded view of an example of a hidden needle assembly.
Figure 20A:
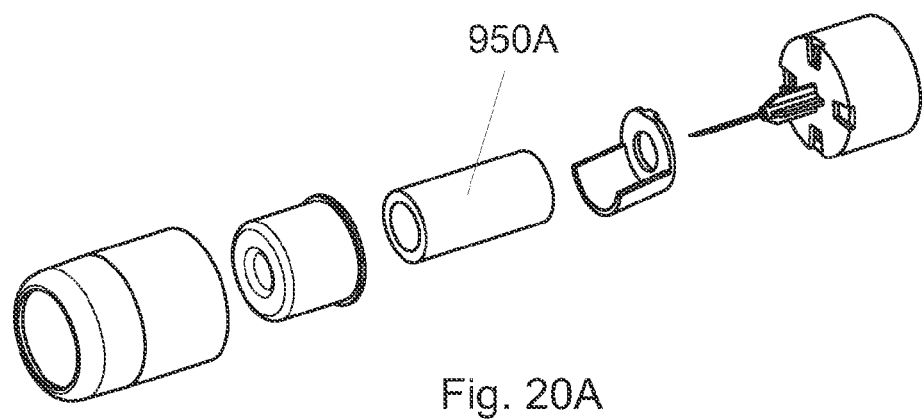
Figure 21C:
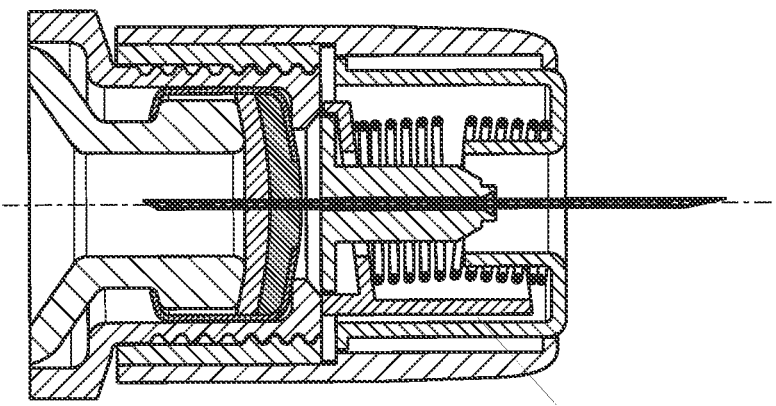
FIG. 21 A-C Show a cross section of the hidden needle assembly of FIG. 20A.
Figure 21B:
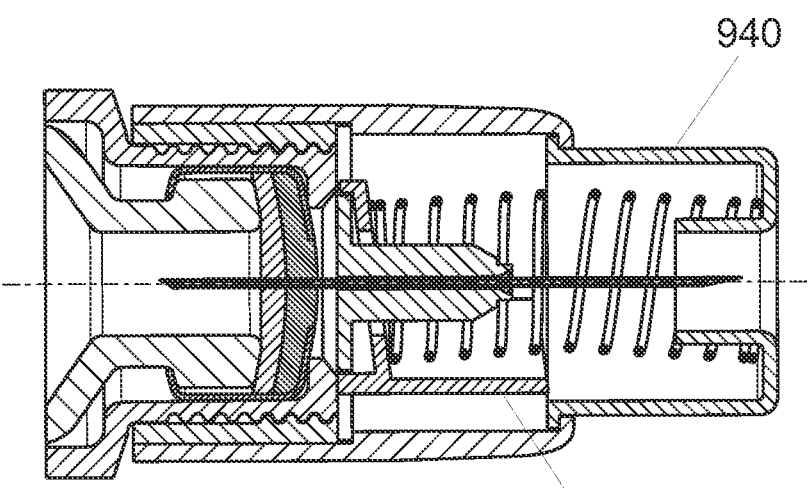
Figure 21A:
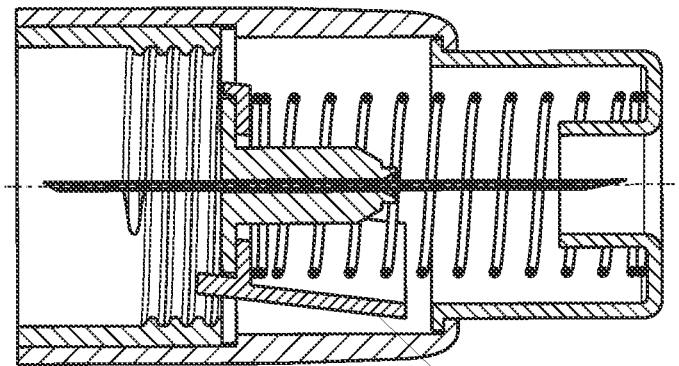
Figure 22:
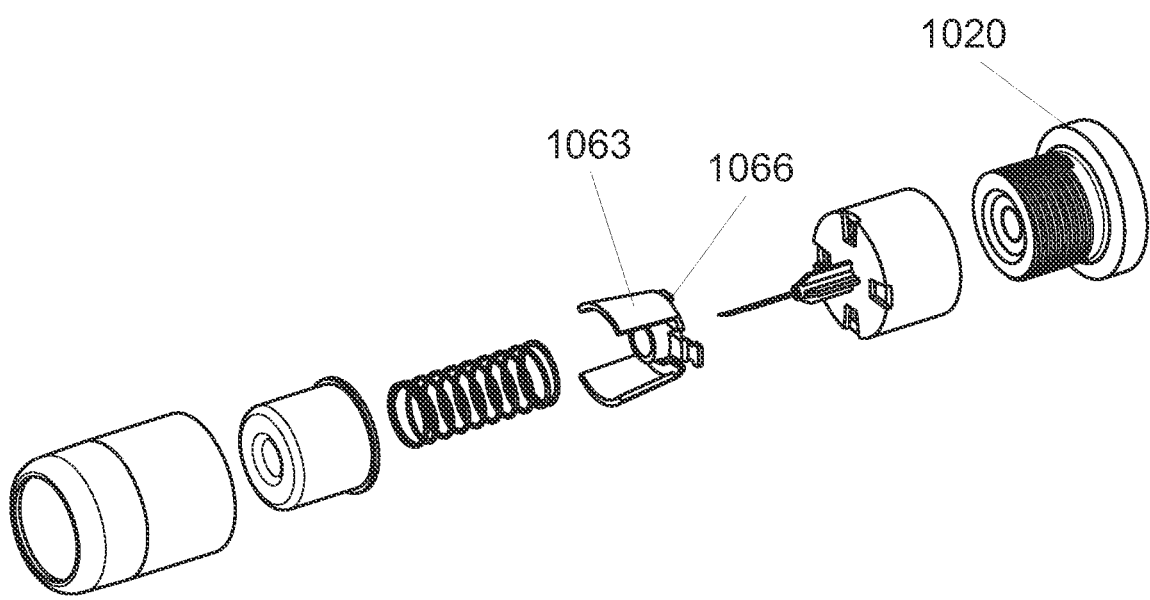
FIG. 22 Show an exploded view of an example of a hidden needle assembly.
Figure 23C:
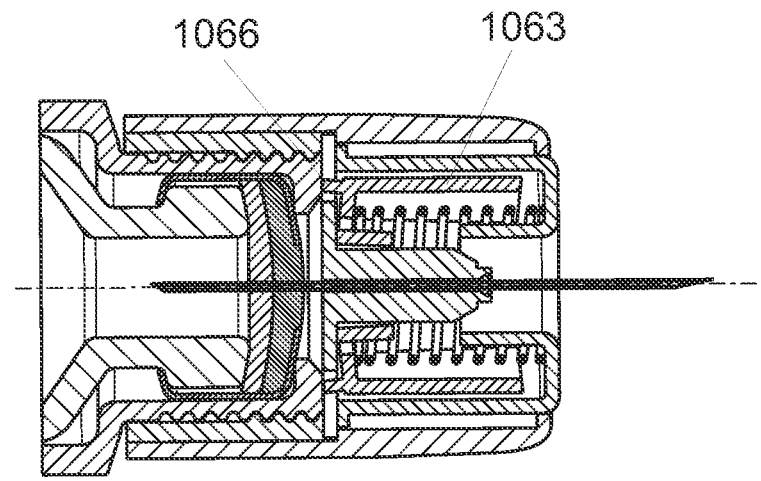
FIG. 23 A-C Show a cross section of the hidden needle assembly of FIG. 22.
Figure 23B:
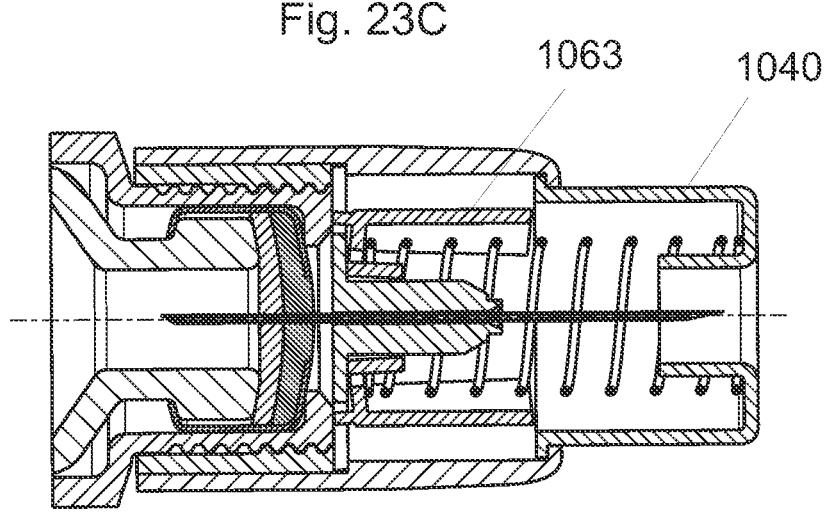
Figure 23A:
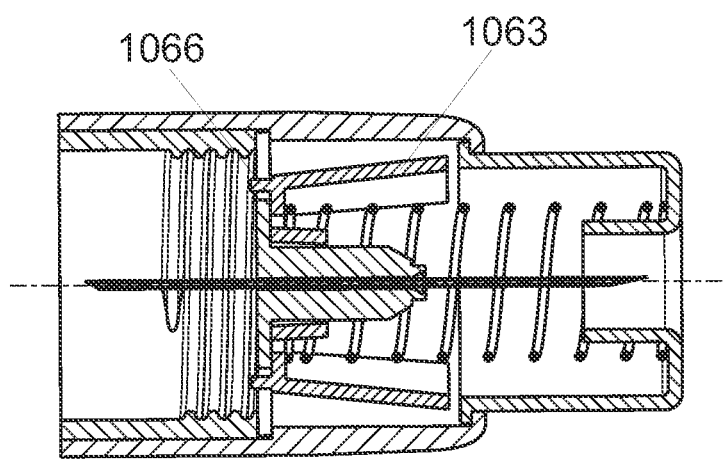
Figure 24C:
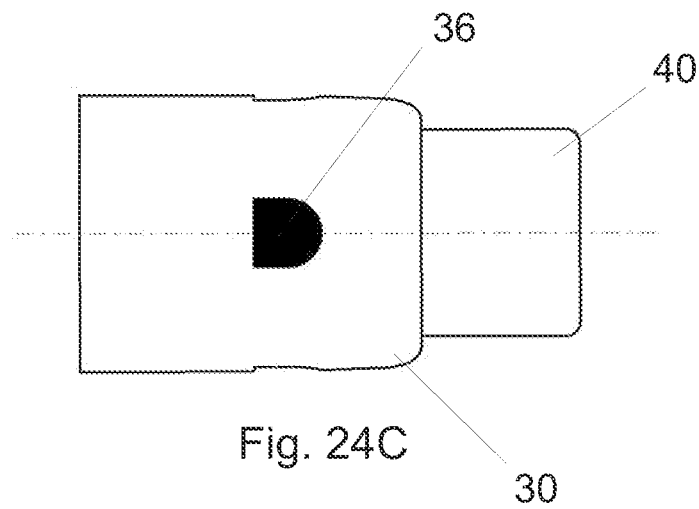
FIG. 24 Show a side view of an example of a hidden needle assembly.
Figure 24B:
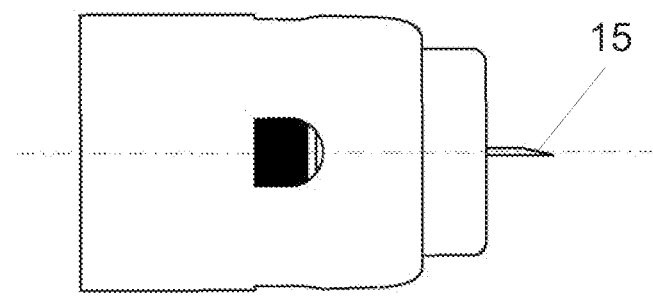
Figure 24A:
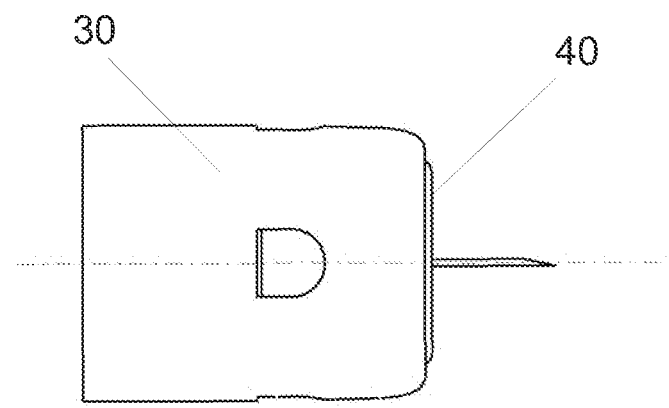

This embodiment discloses a similar needle assembly however, the locking element 960 is only provided with one arm 963. Further, the spring element 950 can be replaced by an elastic sponge 950A as disclosed in FIG. 20A. In fact in any of the embodiments disclosed any element providing a biasing force can be used instead of a spring.

Example 11

FIG. 22-23

In this embodiment the locking element 1060 is provided with two arms 1063 which are deflected inwardly when the fingers 1066 are activated by the injection device attached to the needle assembly.

Example 12

FIG. 24

In all the embodiments the element forming the outer barrier such as the outer shield 30 could be provided with an opening such as a window 36 through which a user can visually see the safety shield 40 or an element moving with the safety shield 40. In this way the user can visually follow the progress of the injection. The element forming the background in the window 40 e.g. the locking member, could be coloured in a different colour than the element passing the window 36 e.g. the safety shield 40 during injection to enhance the visibility of the element passing the window 36.

Example 13

FIG. 25-26

In all the foregoing embodiments the needle assembly could be provided with a mechanism which provides the user with an audible, visual or tactile confirmation when the needle cannula is fully inserted.

Figure 25B:
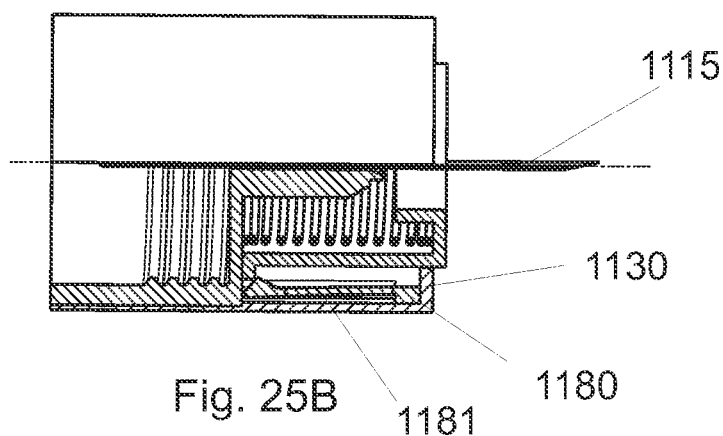
FIG. 25 A-B Show a view of a hidden needle assembly.
Figure 25A:
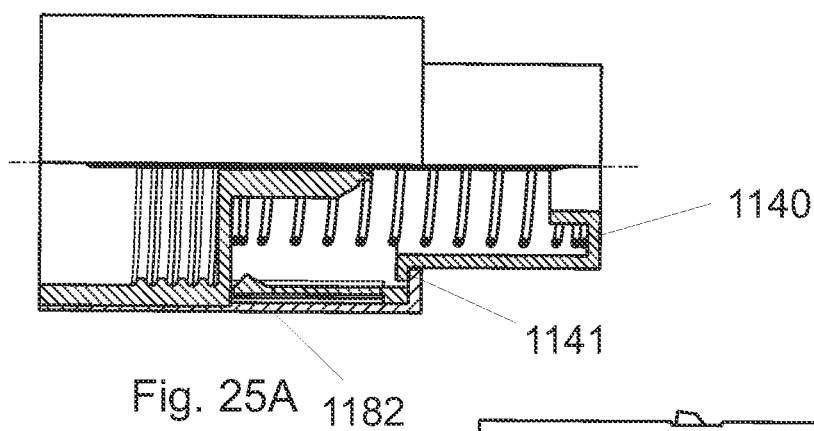

An example of such audible mechanism is disclosed in FIG. 25A-B. Here a mechanism 1180 carrying a click-arm 1181 is provided on the interior of the outer shield 1130, the safety shield 1140 is at its proximal end provided with a peripheral rib 1141 which engages the click-arm 1181 once the safety shield 1140 is pressed fully back in order to provide a distinct sound informing the user that the needle cannula 1115 is fully inserted. This activation can be done in multiple ways e.g. as disclosed by having the click-arm 1181 carry a protrusion 1182 at the end, or the arm 1181 could carry more than one protrusion 1181. The proximal end of the click-arm 1181 could e.g. be formed with a not-shown threaded portion providing a distinct sound as the rib 1141 slides over the threaded portion at the end of the needle insertion. In addition to providing a sound this would also provide a vibration of the needle assembly and the injection device to which it is attached thereby providing a tactile confirmation.

Figure 26B:
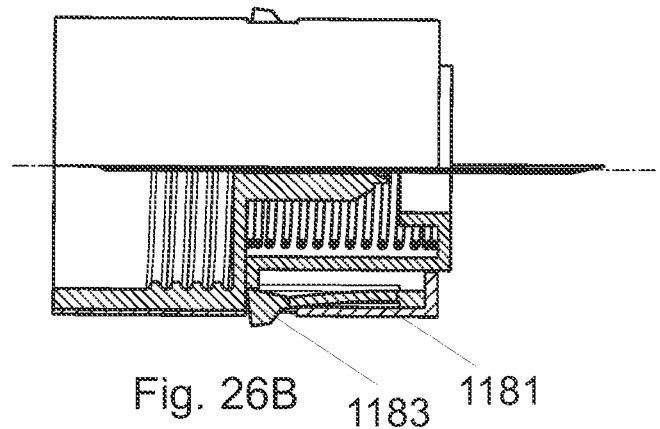
FIG. 26 A-B Show a view of a hidden needle assembly.
Figure 26A:
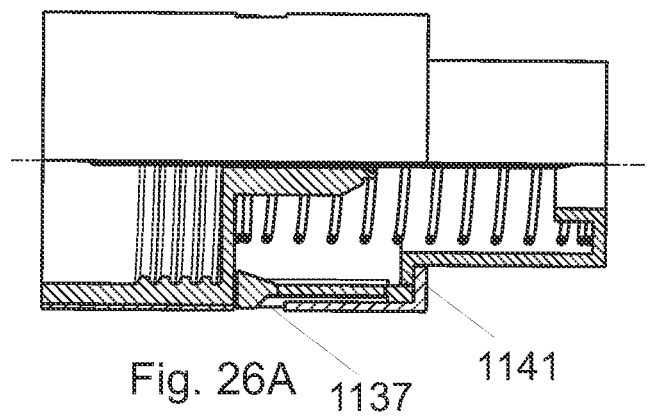

A further example of a visual and tactile indication is provided in the FIGS. 26A-B. In this embodiment the click-arm 1181 is provided with an indicator 1183 e.g. a coloured indicator 1183 which is forced out of an opening 1136 in the outer shield 1130 once the shield reaches its proximal destination. This indicator 1183 could also be provided with a Braille-like indication.

Some preferred embodiments have been shown in the foregoing, but it should be stressed that the invention is not limited to these, but may be embodied in other ways within the subject matter defined in the following claims, e.g. could a needle assembly as herein described be delivered to the user in a rigid and sterile container which further could be shaped as a tool for assisting the user in mounting the needle assembly on to the injection device.

The invention claimed is:

1. A needle assembly for a drug delivery device comprising:
   a needle cannula mounted in a hub adapted to be connected to a drug delivery device via a connecting device of the needle assembly,
   a shield structured to telescopically move from a first position relative to the hub in which a tip of the needle cannula is substantially concealed by the shield, to a second position, in which at least the tip of the needle cannula is exposed,
   a biasing structure urging the shield towards the first position, and
   a releasable locking device structure co-operating with the connecting device of the needle assembly, wherein
   the needle assembly is provided with the releasable locking device structure preventing telescopic movement of the shield and exposure of the tip of the needle cannula if the needle assembly is not mounted to a connecting device of a drug delivery device, and
   the releasable locking device structure of the needle assembly allows telescopic movement of the shield and exposure of the tip of the needle cannula if the needle assembly is mounted to the connecting device of the drug delivery device.

2. A needle assembly according to claim 1, wherein the releasable locking device structure is released when an object such as an injection device is connected to the connecting device of the needle assembly.

3. A needle assembly according to claim 1, wherein the connecting device of the needle assembly is housed in the hub and the releasable locking device has one or more activating parts at least partly located in the area of the hub housing the connecting device of the needle assembly.

4. A needle assembly according to claim 3, wherein the one or more activating parts are fingers protruding into the area of the hub housing the connecting device of the of the needle assembly.

5. A needle assembly according to claim 3, wherein the one or more activating parts are activated when the connecting device of the needle assembly is utilized.

6. A needle assembly according to claim 1, wherein the releasable locking device structure comprises a locking element locking the axial movement of the shield.

7. A needle assembly according to claim 6, wherein the locking element carries locking arms engaging the shield.

8. A needle assembly according to claim 6, wherein the locking element is rotatable relative to the hub.

9. A drug delivery device and needle assembly system comprising:
   a drug delivery device and a needle assembly, each having a connecting device such that the drug delivery device and the needle assembly are structured to connect to each other via the connecting device of the drug delivery device and the connecting device of the needle assembly, wherein
   the needle assembly comprises:
     a needle cannula mounted in a hub having the connecting device for connecting the hub to the drug delivery device,
     a biased shield movable relative to the hub from a first position in which a tip of the needle cannula is substantially concealed by the shield to a second position in which at least the tip of the needle cannula is exposed, and
     a releasable locking device structure co-operating with the connecting device of the needle assembly to lock the shield in the first position, wherein the locking device structure is provided with structure to:
       unlock if the needle assembly is mounted to the connecting device of the drug delivery device allowing movement of the shield relative to the hub, and
       lock if the needle assembly is not mounted to the connecting device of the drug delivery device preventing movement of the shield relative to the hub.

10. A drug delivery device and needle assembly system according to claim 9, wherein the shield can be shifted between a locked and an unlocked position only when the needle assembly is connected to the injection device.

* * * * *